(12) United States Patent
Mizutani et al.

(10) Patent No.: US 7,534,236 B2
(45) Date of Patent: May 19, 2009

(54) INTERLABIAL PAD

(75) Inventors: Satoshi Mizutani, Kagawa (JP); Koichi Yamaki, Kagawa (JP); Yuki Noda, Kagawa (JP); Megumi Tokumoto, Kagawa (JP); Akane Sakai, Kagawa (JP)

(73) Assignee: Uni-Charm Corporation, Kawanoe-Shi, Ehime (JP)

( * ) Notice: Subject to any disclaimer, the term of this patent is extended or adjusted under 35 U.S.C. 154(b) by 392 days.

(21) Appl. No.: 10/705,778

(22) Filed: Nov. 10, 2003

(65) Prior Publication Data
US 2004/0158222 A1    Aug. 12, 2004

Related U.S. Application Data

(63) Continuation of application No. PCT/JP02/04884, filed on May 21, 2002.

(30) Foreign Application Priority Data

May 22, 2001  (JP)  ............................ 2001-152403
Dec. 25, 2001  (JP)  ............................ 2001-392521

(51) Int. Cl.
*A61F 13/15* (2006.01)
(52) U.S. Cl. ............................ 604/385.17; 604/385.01; 604/384; 604/385.03; 604/386
(58) Field of Classification Search ............ 604/385.02, 604/385.17, 385.01, 384, 385.03, 386, 385.04, 604/904, 385.18; D24/141
See application file for complete search history.

(56) References Cited

U.S. PATENT DOCUMENTS

| | | | |
|---|---|---|---|
| 3,989,867 A * | 11/1976 | Sisson | ......................... 428/132 |
| 4,595,932 A | 6/1986 | Ruhl et al. | |
| 5,336,208 A | 8/1994 | Rosenbluth et al. | |
| 5,868,727 A | 2/1999 | Barr et al. | |
| 5,916,205 A | 6/1999 | Olson et al. | |
| 6,131,575 A | 10/2000 | Lenker et al. | |

FOREIGN PATENT DOCUMENTS

CN        1235534 A      11/1999

(Continued)

OTHER PUBLICATIONS

Mizutani, et al., "Flap-Equipped Interlabial Pad", U.S. Appl. No. 10/705,670, Nov. 10. 2003.

(Continued)

*Primary Examiner*—Jacqueline F. Stephens
(74) *Attorney, Agent, or Firm*—Darby & Darby P.C.

(57) ABSTRACT

The present invention concerns an interlabial pad easy to wear between the labia and provides an interlabial pad of a structure allowing to wear between the labia of a woman easily and appropriately.

A mini sheet piece (14) is attached to the opposite side to the body side of the an interlabial pad (1) for constituting a pocket (16) for finger insertion and, at the same time, the shape of a finger insertion opening (19a) constituting the entrance of the pocket (16) is made flat in the planar direction of the sheet so that the boll of the finger can be inserted naturally in contact with the face of the sheet. In addition, the finger insertion opening (19a) is made to guide to a finger application point (3) appropriate for feeling for a wearing point in between the labia.

14 Claims, 21 Drawing Sheets

FOREIGN PATENT DOCUMENTS

| | | | |
|---|---|---|---|
| CN | 1268040 | A | 9/2000 |
| CN | 1268041 | A | 9/2000 |
| EP | 888764 | | 1/1999 |
| JP | 49-3722 | | 1/1974 |
| JP | 61-108258 | | 7/1986 |
| JP | 63260556 | | 10/1988 |
| JP | 03-56366 | | 3/1991 |
| JP | 05237151 | | 9/1993 |
| JP | 05293138 | | 11/1993 |
| JP | 06-506368 | | 7/1994 |
| JP | 6-506368 | A1 | 7/1994 |
| JP | 06-40203 | | 10/1994 |
| JP | 08-215242 | A1 | 8/1996 |
| JP | 2000-51267 | | 2/2000 |
| JP | 200501322 | | 2/2000 |
| JP | 2001-509402 | | 7/2001 |
| JP | 2002-513633 | A1 | 5/2002 |
| JP | 2002-534163 | | 10/2002 |
| TW | 247431 | A1 | 5/1995 |
| TW | 247463 | A1 | 5/1995 |
| TW | 294591 | A1 | 1/1997 |
| TW | 338315 | A1 | 8/1998 |
| TW | 386030 | A1 | 4/2000 |
| TW | 386872 | A1 | 4/2000 |
| TW | 394681 | A1 | 6/2000 |
| TW | 416847 | A1 | 1/2001 |
| TW | 442278 | A1 | 6/2001 |
| TW | 450802 | A1 | 8/2001 |
| TW | 454503 | A1 | 9/2001 |
| TW | 470640 | A1 | 1/2002 |
| TW | 524677 | A1 | 3/2003 |
| WO | 92/11825 | A1 | 7/1992 |
| WO | WO-94/21531 | A1 | 9/1994 |
| WO | WO-95/00094 | | 1/1995 |
| WO | WO-95/17148 | A2 | 6/1995 |
| WO | WO 98/08475 | * | 3/1998 |
| WO | WO-98/08475 | A1 | 3/1998 |
| WO | WO-99/01093 | A1 | 1/1999 |
| WO | WO-99/01096 | A1 | 1/1999 |
| WO | 99/56681 | | 11/1999 |
| WO | WO-99/56689 | A1 | 11/1999 |
| WO | 00/40192 | | 7/2000 |
| WO | WO-01/47458 | | 7/2001 |

OTHER PUBLICATIONS

Mizutani, et al., "Interlabial Pad and Package Thereof", U.S. Appl. No. 10/705,810, Nov. 10, 2003.
Mizutani, Satoshi, "Interlabial Product Having Form for Finger Securement, and Individual Package", U.S. Appl. No. 10/705,779, Nov. 10, 2003.
Mizutani, et al., "Interlabial Pad", U.S. Appl. No. 10/705,408, Nov. 10, 2003.
Mizutani, et al., "Interlabial Pad Individual Packaging Vessel", U.S. Appl. No. 10/705,673, Nov. 10, 2003.
Mizutani, et al., "Interlabial Pad", U.S. Appl. No. 10/705,780, Nov. 10, 2003.
Mizutani, et al., "Interlabial Pad and Package Thereof", U.S. Appl. No. 10/705,404, Nov. 10, 2003.
Mizutani, et al., "Interlabial Pad and Package Thereof", U.S. Appl. No. 10/705,400, Nov. 10, 2003.
Mizutani, et al., "Interlabial Pad and Package", U.S. Appl. No. 10/706,303, Nov. 10, 2003.
Mizutani, et al., "Interlabial Pad Individual Packaging Body", U.S. Appl. No. 10/705,669, Nov. 10, 2003.
Mizutani, et al., "Interlabial Pad", U.S. Appl. No. 10/705,407, Nov. 10, 2003.
Mizutani, et al., "Interlabial Pad", U.S. Appl. No. 10/705,811, Nov. 10, 2003.
Mizutani, et al., "Interlabial Pad", U.S. Appl. No. 10/705,403, Nov. 10, 2003.
Mizutani, et al., "Interlabial Pad", U.S. Appl. No. 10/705,812, Nov. 10, 2003.
Mizutani, et al., "Individual Packaging Body and Outer Vessel Therefor", U.S. Appl. No. 10/705,402, Nov. 10, 2003.
Mizutani, et al., "Interlabial Pad", U.S. Appl. No. 10/705,399, Nov. 10, 2003.
Mizutani, et al., "Interlabial Pad Individual Packaging Vessel, and Individual Packaging Body", U.S. Appl. No. 10/705,781, Nov. 10, 2003.
Mizutani, et al., "Flap-Equipped Interlabial Pad", U.S. Appl. No. 10/705,670, Nov. 10, 2003.
Mizutani, et al., "Interlabial Pad and Package Thereof", U.S. Appl. No. 10/705,810, Nov. 10, 2003.
Mizutani, et al., "Interlabial Pad", U.S. Appl. No. 10/705,406, Nov. 10, 2003.
Mizutani, Satoshi, "Interlabial Product Having Form for Finger Securement, and Individual Package", U.S. Appl. No. 10/705,779, Nov. 10, 2003.
Mizutani, et al., "Interlabial Pad", U.S. Appl. No. 10/705,408, Nov. 10, 2003.
Mizutani, et al., "Interlabial Pad Individual Packaging Vessel", U.S. Appl. No. 10/705,673, Nov. 10, 2003.
Mizutani, et al., "Interlabial Pad", U.S. Appl. No. 10/705,780, Nov. 10, 2003.
Mizutani, et al., "Interlabial Pad and Package Thereof", U.S. Appl. No. 10/705,404, Nov. 10, 2003.
Mizutani, et al., "Interlabial Pad and Package Thereof", U.S. Appl. No. 10/705,400, Nov. 10, 2003.
Mizutani, et al., "Interlabial Pad and Package", U.S. Appl. No. 10/706,303, Nov. 10, 2003.
Mizutani, et al., "Interlabial Pad Individual Packaging Body", U.S. Appl. No. 10/705,669, Nov. 10, 2003.
Mizutani, et al., "Interlabial Pad", U.S. Appl. No. 10/705,407, Nov. 10, 2003.
Mizutani, et al., "Interlabial Pad", U.S. Appl. No. 10/705,811, Nov. 10, 2003.
Mizutani, et al., "Interlabial Pad", U.S. Appl. No. 10/705,403, Nov. 10, 2003.
Mizutani, et al., "Interlabial Pad", U.S. Appl. No. 10/705,812, Nov. 10, 2003.
Mizutani, et al., "Individual Packaging Body and Outer Vessel Therefor", U.S. Appl. No. 10/705,402, Nov. 10, 2003.
Mizutani, et al., "Interlabial Pad", U.S. Appl. No. 10/705,399, Nov. 10, 2003.
Mizutani, et al., "Interlabial Pad Individual Packaging Vessel, and Individual Packaging Body", U.S. Appl. No. 10/705,781, Nov. 10, 2003.
European Search Report, Sep. 10, 2004, EP 02 77 1745.
Office Action for EP Application No. 02 771 747.9-1217, Examiner Florence Joly, dated Nov. 8, 2007.
Office Action for EP Application No. 03 795 252.0-2124, Examiner Silvia Gennari, dated Nov. 2, 2007.
Office Action for EP Application No. 02 771 742.0-1217, Examiner Florence Joly, dated Nov. 8, 2007.

* cited by examiner (A)

(B)

⇩

(C)

(D)

(A)

(B)

(C)

(A)

(B)

(A)

(B)

(C)

(A)

(B)

(A)

(B)

(C)

(A)

(B)

(A)

(B)

INTERLABIAL PAD

CROSS-REFERENCE TO RELATED APPLICATIONS

This application is a Continuation of International Application No. PCT/JP02/04884 filed May 21, 2002, which application published in Japanese on Nov. 28, 2002 as WO 02/094148 A1 under PCT Article 21(2).

BACKGROUND OF THE INVENTION

1. Technical Field

The present invention relates to an interlabial pad that can be worn easily between labia.

2. Background Art

Conventionally, a sanitary napkin and a tampon are used generally as a female sanitary product. Here, there have been great efforts to prevent the leak of menstrual blood from a gap caused by poor adhesion near the ostium vaginae as for the sanitary napkin. Moreover, as for the tampon, there have been great efforts for relieving a foreign feeling and discomfort when the sanitary product is worn and for lowering difficulty in intervaginal wearing due to the nature of the product.

Under such situation, an interlabial pad have attracted people as a sanitary product positioned between the sanitary napkin and the tampon in recent years.

The interlabial pad is used by inserting a portion of it between the labia and brought into contact with an inner face of labia, and prevents the menstrual blood from leaking because of higher adhesion to the body than that of the sanitary napkin and the menstrual blood from widely contacting with the body due diffusion so that it is sanitary and clean. Moreover, the interlabial pad has characteristics that it excels in a wearing feeling, is comfortable because of being smaller than the sanitary napkin and that it has lower psychological resistance on wearing than that of the tampon which is inserted into the vagina.

However, compared to the sanitary napkin, the interlabial pad is more difficult to be worn than the sanitary napkin, because it is worn between the labia, which are difficult to be seen. Moreover, if it is not fitted to an appropriate position, leakage damage tends to be considerable, because it is smaller than the sanitary napkin in size. Also, compared to the tampon, there is higher possibility of in proper wearing than the tampon.

As an example of improvement in wearing such interlabial pad, PCT International Publication No. WO99/56689 discloses one having a structure composed of a projection 60 on a surface opposed to the surface in contact with the body. According to this structure, as the wearer can wear by pinching the projection with fingers, it is conceivable that the wearing is easier that the case without projection (refer to FIG. 35 (corresponding to FIG. 1 in the aforementioned Publication)).

However, in such a structure, as the wearer feels for the wearing point with her nail tips, the wearer actually is obliged to wear it with her intuition so that it is not easy for the wearer to locate the right wearing point. Especially, if the wearer has long nails or wears fake nails, it is extremely difficult to wear the aforementioned interlabial pad or the like of the prior art to the right position. In addition, it is difficult to apply the interlabial pad into the labia with a satisfactory contact only by using the pinched projection 60.

Therefore, the aforementioned interlabial pad of the prior art does not come to facilitate the wearing by locating the right wearing point, reduce the occasion of mis-wearing or realize a satisfactorily close contact with the genital area. Moreover, still menstrual blood or others may attach to finger tips during the wearing, constituting one of factors causing the reluctance of using the interlabial pad.

DISCLOSURE OF THE INVENTION

The present invention has been devised considering the aforementioned problems and has an object of providing an interlabial pad composed to facilitate a secure and hygienic wearing between female labia.

In order to solve the aforementioned problems, the present invention concerns a interlabial pad provided with a structure allowing to wear, in a sufficiently close adherence to the genital area, all the way securing the wearing point by using a ball of fingertips having a keen tactile sensation, and more particularly, an interlabial pad comprising a pocket provided on the backside of the pad and where the finger tip can be inserted smoothly, and allowing to wear between the labia in a state where a finger is inserted there.

To be more specific, the present invention provides those like as follows.

(1) An interlabial pad formed into a substantial rectangle having a longitudinal direction and a lateral direction provided with a size, weight and flexibility allowing to be pinched and held partially or totally in between labia without forcing, the interlabial pad comprising:

a body side face orientated to a body side and an opposite side face to the body side orientated to a garment side;

a mini-sheet striding from one portion to another portion at each side portion of both sides in the longitudinal direction of the interlabial pad as a central axis; and a finger insertion opening formed between the mini-sheet and said opposite side face to the body side, for directly securing the opening of the fingerbreadth of a wearer;

wherein said mini-sheet is disposed in a way to cover at least a portion (finger application point) of said opposite side face to the body side corresponding to an area (application point) of said surface side sheet applied to a predetermined position between the labia of the wearer; and wherein said finger insertion opening serves for guiding a fingertip of the wearer to an application point.

The interlabial pad according to the present invention has a mini-sheet disposed on the opposite side to the body side. This mini-sheet is linked to the interlabial pad at both edges corresponding to the longitudinal direction of the interlabial pad; however, at both edges (both sleeves) corresponding to the lateral direction of the interlabial pad, at least one sleeve is not linked to the opposite side face to the body side of the interlabial pad. This non-linked portion forms a cuff between one sleeve of the mini-sheet and the opposite side face to the body side, and such cuff serves as a finger insertion opening where a finger can be inserted (refer to FIG. 6(A), FIG. 19).

Besides, the mini-sheet is provided in a state striding from one side to the other side of the interlabial pad, and the right and left sides of the interlabial pad is linked to the mini-sheet, but it is not linked (glued) inside the inner edge. Consequently, in such portion striding from one side to the other side, a space (finger insertion space) allowing to hold the interlabial pad at a fingertip by inserting a finger comes to be formed. Such structure permits the wearer to insert a finger from the aforementioned finger insertion opening into the finger insertion space, and to hold interlabial pad temporarily at the fingertip.

Moreover, according to the present invention, the finger insertion opening is composed as an opening of the size corresponding to the fingerbreadth, namely, the width of a finger in the direction of the nail width and not the thickness of a finer. Consequently, a finger is inserted with the fingertip having a flat shape naturally in contact with the opposite side face to the body side, and not in a different direction in respect to the opposite side face to the body side. In short, as the finger insertion opening is formed large laterally in the planer direction of the opposite side face to the body side copying the fingertip shape of the wearer, the insertion direction of a finger of the wearer comes to be specified, inducing the wearer to feel for the wearing point with the ball of a fingertip.

In this respect, Japanese Patent Publication No. Hei 6-506368 discloses an incontinence prevention pad wherein a bag shape finger hole is provided on the opposite side to the body side. This finger being described to be "crushed in the normal state, but extended when a finger is inserted", first, the finger is inserted in a direction making a right angle with the incontinence prevention pad (refer to FIG. 37 (corresponding to FIG. 22 in the Publication)), because the finger hole 70 (symbol 76 in the Publication) is closed in the normal state (refer to FIG. 36 (corresponding to FIG. 20 in the Publication)), and thereafter, the ball of the finger can face the incontinence prevention pad side only when the finger is turned.

In order to perform such operation, it is necessary to fix the incontinence prevention pad by one hand and, if it is not the case, the incontinence prevention pad turns with the finger, preventing to set the finger at a desired position. Consequently, in the aforementioned incontinence prevention pad, the fitting operation to a fingertip comes to be troublesome and burdensome.

As obvious from the foregoing, the finger hole provided on said incontinence prevention pad can not have a satisfactory effect of easy and rapid wearing, because the finger insertion direction is specified to make a right angle with the sheet surface.

On the contrary, the finger insertion opening provided on the interlabial pad according to the present invention "secures directly" an opening of fingerbreadth to the opposite side face to the body side. This "secures directly" means that the interlabial pad itself is composed to take primarily a form appropriate for inserting a finger, in case of inserting the finger naturally into the interlabial pad in order to wear the interlabial pad (in case of inserting a finger as it is, facing the ball of the finger to the sheet face of a sheet disposed on the opposite side face to the body side of the interlabial pad, in the present invention) and, cases of forming secondarily an opening of fingerbreadth on the planar direction of the back side sheet as the case of securing an opening of fingerbreadth in the planar direction by turning the finger after the insertion thereof by the wearer are excluded. In short, according to the present invention, a holding state of interlabial pad at the fingertip appropriate for wearing the interlabial pad can be secured immediately.

Moreover, according to the present invention, it is so composed that the fingerprint surface of a finger inserted from the finger insertion opening is positioned at a finger application point, namely, a point corresponding to the point (application point) appropriate for feeling for the best place for wearing the interlabial pad, on the opposite side face to the body side of the interlabial pad (refer to FIG. 6(C)). Therefore, even for a wearing between the labia difficult to observe, it becomes possible to wear the interlabial pad on an appropriate position, by accurately grasping the correct wearing point.

For the mini-sheet in the present invention, in addition to a separate attachment of a member different from the body of the interlabial pad, it may be formed in a portion extending from a part of the body of the interlabial pad. It should be appreciated that the point of attachment of a mini-sheet composed of a different member includes not only the portion corresponding to the periphery of the interlabial pad, but also the vicinity of the periphery where the mini-sheet can be joined. Consequently, in the present Description, the "side portion" in the longitudinal direction of the interlabial pad includes not only the portion corresponding to the periphery of the interlabial pad, but also the vicinity of the periphery where the mini-sheet can be joined.

Also, it results in that the "edge portion" in the mini-sheet includes not only the portion corresponding the outer edge of the mini-sheet, but also the vicinity of the outer edge that can be joined to the opposite side face to the body side of the interlabial pad.

In order to facilitate the wearer to identify the mini-sheet, the mini-sheet can be adjusted to have color tone, pattern, chromaticity different from the backside sheet of the interlabial pad, using a method such as coloring, pattern print, or others.

For the present invention, in the opposite side face to the body side of the interlabial pad, the side edge of the mini-sheet is linked in the longitudinal direction, but at least one sleeve is not joined in the lateral direction. Here, in case where both sleeves of the mini-sheet are not joined in the lateral direction of the opposite side face to the body side of the interlabial pad, said finger insertion space becomes a through-hole (tunnel state). On the other hand, in case where one sleeve of the mini-sheet, said finger insertion space turns to be non perforated cavity state.

It should be appreciated that, in the present Description, "orientated" means that the quater is distributed in a predetermined direction.

(2) The interlabial pad of claim (1), wherein said mini-sheet is disposed biased to one end in said longitudinal direction of said interlabial pad.

The interlabial pad according to the present invention allows to position a mini-sheet in a position where the fingertip is covered with the mini-sheet, when the wearer inserts her finger from a finger insertion opening formed with the mini-sheet into a following space (finger insertion space) even when the portion of the mini-sheet not bonded to the opposite side face to the body side of the interlabial pad is provided in the finger insertion direction as a second non-bonded portion other than a first non-bonded portion forming the finger insertion opening.

Consequently, the fingertip inserted in the finger insertion space is not exposed, reducing the occurrence of contact between the fingertip and menstrual blood remaining on the labia. Especially, in case where the mini-sheet has a length as mentioned below in (7), the fingertip would not slip out from the interlabial pad, and the mini-sheet can be made to cover the fingertip securely.

It should be appreciated that, in case where the number of mini-sheet is plural, the effect of the present invention can be exhibited, if the mini-sheet positioned at the extremity of the finger insertion direction is positioned so that the non-bonded portion positioned at the extremity of the finger insertion direction corresponds to the aforementioned second non-bonded portion.

(3) The interlabial pad of claim (1) or (2), wherein said mini-sheet is disposed on said opposite side face to the body side of said interlabial pad, in a way to form a pocket shape finger insertion space.

In the interlabial pad according to the present invention, the mini-sheet is bonded to the opposite side face to the body side of the interlabial pad in the outer edge portion except the edge forming the finger insertion opening. Therefore, in the portion in contact with the extremity of the finger inserted from the finger insertion opening, the opposite side face to the body side and the mini-sheet turn to be adhered, avoiding such a situation that the extremity portion of the finger runs out without being covered with the mini-sheet. Furthermore, the contact between the fingertip of the wearer and menstrual blood or labia is prevented completely, such a situation that menstrual blood enters the finger insertion space, permitting to make it more hygienic than that in the aforementioned (2).

It should be appreciated that, in the present Specification, a "pocket" means a bag shape member where a finger can enter entirely and smoothly and, preferably, the cross sectional shape thereof is flat or similar to it; however, other than the same, semicylindrical one or others can be adopted, and it is not limited to the same.

(4) The interlabial pad of any one of claims (1) to (3), wherein at least a part of said mini-sheet is stretchable or elastically extensible at least in respect to said lateral direction of said interlabial pad.

In the interlabial pad according to the present invention, the mini-sheet is distensible or elastically stretchable at least in the lateral direction of the opposite side face to the body side of the interlabial pad. Consequently, even when the size of the fingertip of the wearer is bigger than the predetermined finger insertion opening, the interlabial pad according to the present invention comes to be able to be used effectively, independently of the finger tip size of the wearer, because the mini-sheet extends at least in the fingerbreadth direction according to the size of the finger.

It should be appreciated that, in the present Description, "at least a part" of the mini-sheet means to include also a case where only a portion of the mini-sheet is distensible or elastically stretchable, in addition to the case where the whole mini-sheet is distensible or elastically stretchable.

(5) The interlabial pad of any one of claims (1) to (4), wherein said mini-sheet has a bonding portion in a portion striding across said opposite side face to the body side.

In the interlabial pad according to the present invention, a bonding portion is disposed on the mini-sheet provided in the opposite side face to the body side. As such, for instance, those interlabial pads wherein the interlabial pad is composed as an interlabial pad with a flap portion comprising a pair of flap portions at a pair of both side edges taking the longitudinal direction as a central axis, the pair of flap portions are folded to the opposite side to the body side of the interlabial pad, and the portion where the end of the pair of flap portions and the vicinity of the end are superposed is bound for forming a finger insertion space between the flap portion and the opposite side face to the body side of the interlabial pad can be cited.

Said superposed potion can be bonded not only by adhesion by means of glue, heat seal or the like, but also in non adhesion state. In case of bonding the superposed portion in non-adhesion state, there is a method for engaging both terminal portions by notching the terminal portion of the both, or by partially folding the terminal portion.

It should be appreciated that, for the pair of flap portions, the bonding portion can also be made redetachable, and adjustable as required during use. In addition, it is also possible to make the flap portion non-bonded during the distribution stage, so that each wearer can bind respectively before the use to form a finger insertion opening according to the size of her own finger.

(6) The interlabial pad of any one of claims (1) to (5), wherein said interlabial pad is composed by bonding a surface side sheet disposed on said body side face of the interlabial pad and a back side sheet disposed on said opposite side face to the body side, in a state of containing said absorbent body; and wherein said mini-sheet is attached to said interlabial pad by bonding another sheet separately to a side of said both sides of said interlabial pad in a portion other than the portion where said surface side sheet and said back side sheet are bonded.

In the interlabial pad according to the present invention, a mini-sheet is attached to a point different from the portion where said face side sheet and said back side sheet are bonded. Consequently, the aforementioned bonding portion can be made to have a thinner and softer feel that a structure attaching a mini-sheet to the point where a side sheet and a back side sheet are bonded. Especially, when the bonding portion of said face side sheet and said back side sheet is disposed in the periphery of the interlabial pad, the present invention turns to be extremely useful, because such periphery may come into contact with the femoral region of the wearer.

In this case, a situation where only the attachment portion moves can be prevented, by setting the potion of the attachment portion to the back side sheet of the mini-sheet more inside that said periphery.

In the present invention, the mini-sheet may be cut previously to adapt to the aforementioned attachment portion, or the attachment position may only be made different from the other sheet, and cut with the other sheet.

(7) The interlabial pad of any one of claims (1) to (6), wherein said mini-sheet has a length dimension equal or superior to 10% in respect to said longitudinal direction of said interlabial pad.

The interlabial pad according to the present invention allows sustaining a state at the moment of finger insertion from a finger insertion opening formed with the mini-sheet into a following space (finger insertion space), until wearing the interlabial pad between the labia. In short, as the mini-sheet forming the finger insertion space has a constant size, the finger, once inserted in the finger insertion space, does not slip off, nor move in the finger insertion space, and the ball of the finger is kept face to the opposite side face to the body side of the interlabial pad. Thereby, as the finger can be held stably in the interlabial pad, the interlabial pad can be fitted in the same direction as the longitudinal direction of the cunnus further easily.

In addition, in the interlabial pad according to the present invention, the fact that the mini-sheet has a constant length turns to specify the finger insertion direction. Therefore, the mini-sheet in the present invention plays also a role of suggesting the finger insertion direction.

(8) The interlabial pad of any one of claims (1) to (7), wherein a length of a depth in the finger insertion direction from said finger insertion opening is longer than a length from a fingertip of an index or middle finger of an ordinary woman to a second joint.

In the interlabial pad according to the present invention, the length in the finger insertion direction of the mini-sheet is more preferable for the wearer to hold and operate the interlabial pad by her finger, independently of size, shape and number of the mini-sheet. Consequently, the wearer comes to be able of wearing the interlabial pad more smoothly.

(9) The interlabial pad of any one of claims (1) to (8), wherein a total circumferential length of an inside of said finger insertion opening is between 30 mm and 120 mm, or more preferably between 40 mm and 80 mm.

In the interlabial pad according to the present invention, the finger insertion opening has a magnitude preferable for the circumference of the middle of finger of the wearer.

In this respect, in case where the inner total circumference of the finger insertion opening is shorter than 30 mm, the finger insertion opening itself becomes small, and impedes finger insertion/extraction. On the other hand, if it is longer than 120 mm, the interlabial pad is not fixed on the finger, preventing the ball of the finger from adhering securely to the sheet surface, and the wearing becomes troublesome.

On the contrary, in case where the inner total circumference of the finger insertion opening is set to the dimension of the present invention, the finger can be inserted in and extracted from the finger insertion opening easily, and at the same time, the wearing of interlabial pad can be facilitated all the way keeping the finger inserted in the finger insertion opening.

(10) The interlabial pad of any one of claims (1) to (9), wherein said opposite side face to the body side of said interlabial pad is provided with extremely fine concave and convex.

In the interlabial pad according to the present invention, said opposite side face to the body side is provided with extremely fine concave and convex. Consequently, when the interlabial pad is held by the fingertip, the contact area between the ball face of the fingertip and the opposite side face to the body side is reduced, avoiding phenomena such as friction or sticking between the fingertip and the interlabial pad. Thereby, a situation where the interlabial pad is fitted to a place out of the intention of the wearer under the influence of the state of the finger of the wearer, for instance, a wet surrounding, can be avoided. In addition, as the finger can be extracted smoothly after the wearing, the displacement after the wearing can be prevented.

It should be appreciated that it is desirable to dispose the aforementioned extremely fine concave and convex, most advantageously all over the opposite side face to the body side of the interlabial pad, preferably in the finger insertion space, and at least at the finger application point.

(11) The interlabial pad of any one of claims (1) to (10), wherein an adhesive is applied to a portion of a skin contact surface defined as a portion in contact with the skin of the wearer when said interlabial pad is worn, in said opposite side face to the body side of said interlabial pad.

In the interlabial pad according to the present invention, a pressure sensitive adhesive is applied previously to a portion of the body side face. By doing this, it becomes possible to adhere the interlabial pad firmly between the labia or to the pudenda, allowing to prevent a gap from being created between the interlabial pad and the body even when the wearer changes her posture suddenly. Therefore, the wearer can move her body freely and securely without her motion being restricted.

(12) The interlabial pad of any one of claims (1) to (11), wherein an upheaval area protruding toward the body side exists at the central portion of the lateral direction of the body side face on said body side face of the interlabial pad.

In the interlabial pad according to the present invention, an upheaval area convex toward the body side is formed on the body side face. Then, a finger application point for engaging this upheaval area securely in the labia is provided. Consequently, it becomes possible to engage the convex upheaval area provided previously in the body side face appropriately between the labia, be feeling exactly for an interlabial recess with the ball of the finger (especially fingerprint portion) having an excellent tactile sensation. Thereby, it becomes possible to enhance the adhesion between the body and the interlabial pad, and reduce an external leak of menstrual blood.

It should be appreciated that, substantial flat areas except for the upheaval area being positioned to cover the pudenda when the interlabial pad is worn, it becomes possible to shut a lateral leak of menstrual blood.

Thus, the interlabial pad of the present invention, providing wearing facility, wearing state maintenance and adherence at the same time, is remarkably different from the other sanitary products presenting a similar appearance at a glance, without providing these effects simultaneously, for instance, sanitary napkin merely protruding a part of the face in contact with the body, such as disclosed in Japanese Utility Model Publication No. HEI5-18523.

It should be appreciated that the upheaval can be formed not only by superposing absorbent bodies, but also by folding the interlabial pad taking the longitudinal direction as central axis.

(13) The interlabial pad of any one of claims (1) to (12), wherein said opposite side face to the body side of said interlabial pad is made of moisture permeable material.

In the interlabial pad according to the present invention, the opposite side face to the body side of said interlabial pad is composed of a moisture permeable material. Consequently, the moisture during the wearing can be reduced, and the discomfort of the wearer when she wears the interlabial pad can be reduced.

(14) The interlabial pad of any one of claims (1) to (13), wherein the pad is composed of biodegradable material and/or water-soluble material and/or water dispersible material.

The interlabial pad according to the present invention, being composed of biodegradable material and/or water dispersible material and/or water-soluble material, ends up to be decomposed naturally as it is chronically or positively after the use. Consequently, it turns up to be disposable as it is in a water closet after the use, allowing to discard used interlabial pads simply and hygienically. In other words, in order to discard an interlabial pad, the wearer simply goes to the bathroom, spreads between her thighs towards the toilet and lets the interlabial pad fall from between the labia into the toilet; so the wearer is released from a troublesome operation of discarding the used product using her hand expressly. In addition, it allows advantageously planning to reduce trash left in the toilet.

(15) The interlabial pad of any one of claims (1) to (14), wherein said interlabial pad is an interlabial pad for incontinence.

The interlabial pad according to the present invention can be used as an absorbing pad for incontinence. In short, in case of using the interlabial pad according to the present invention pinched between the labia, it can absorb urine, because both the ostium vaginae for discharging menstrual blood and the urethral meatus for discharging urine are located between the labia.

Thus, according to the present invention, an absorbing pad particularly useful for incontinence and especially a light incontinence can be obtained, because urine can be absorbed between the labia, particularly in the proximity of the urethral meatus.

(16) The interlabial pad of any one of claims (1) to (14), wherein said interlabial pad is an interlabial pad for absorbing vaginal discharge.

In the interlabial pad according to the present invention, the interlabial pad can be used for absorbing virginal discharge. In short, as the interlabial pad according to the present invention is used by being pinched between the labia, it can absorb excretion from the ostium vaginae other than menstrual blood (virginal discharge), and can also be used for this application (absorption of virginal discharge).

Thus, according to the present invention, the discomfort of the wearer can be mitigated by absorbing virginal discharge, making it effective also for the wearer who is not menstruating.

(17) An interlabial pad manufacturing method for manufacturing the interlabial pad recited in (5), comprising the steps of:

setting a pair of wings, longer than usual, the wings being ordinarily disposed at both side portions of a sanitary napkin; and bonding said wings to form said mini-sheet.

According to the present invention, a finger insertion space is formed by providing the interlabial pad with wings adopted for an ordinary sanitary napkin or others by setting slightly longer, and bonding the wings set slightly longer each other. Therefore, a process which is normally used for the sanitary napkin can be used for the interlabial pad so that the interlabial pad that can be worn in the right and easy manner, may be manufactured.

BEST MODE OF CARRYING OUT THE INVENTION

Figure 1:
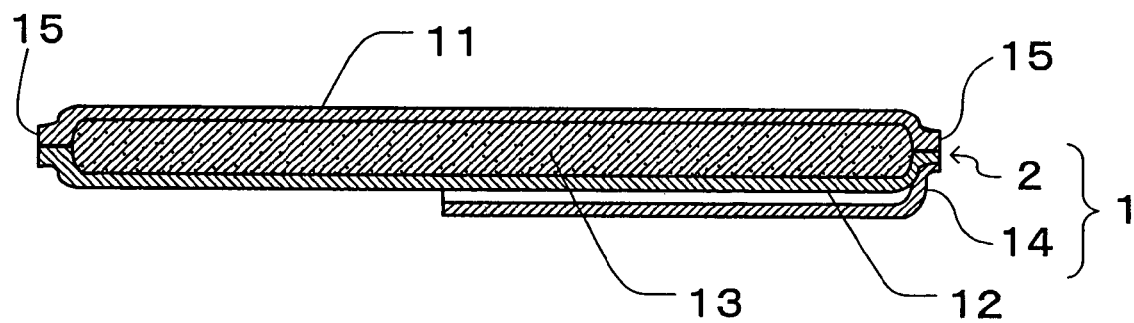
FIG. 1 shows an inner composition of an interlabial pad of a first embodiment.

Next, embodiments of the present invention shall be described referring to the drawings.

First Embodiment

Figure 2:
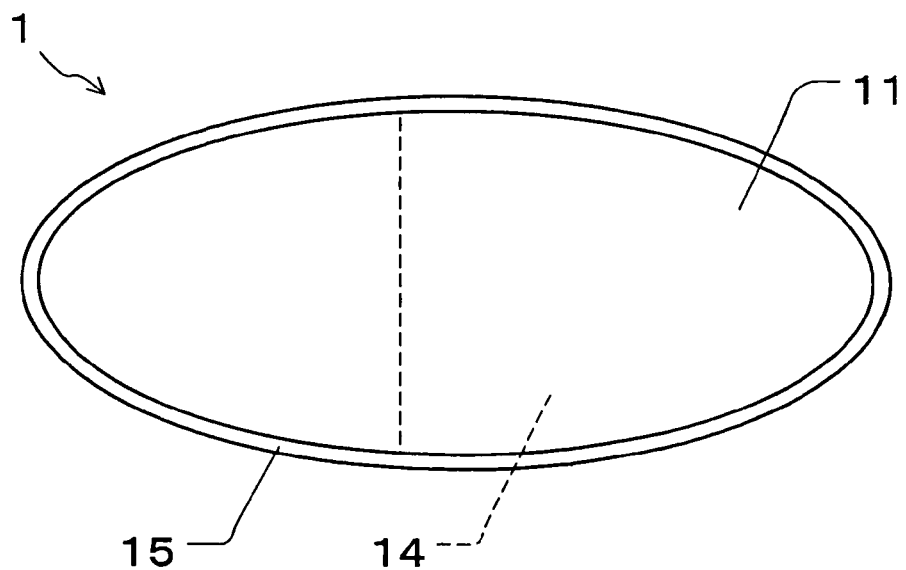
FIG. 2 shows a surface (body side) of the interlabial pad of the first embodiment.
Figure 3:
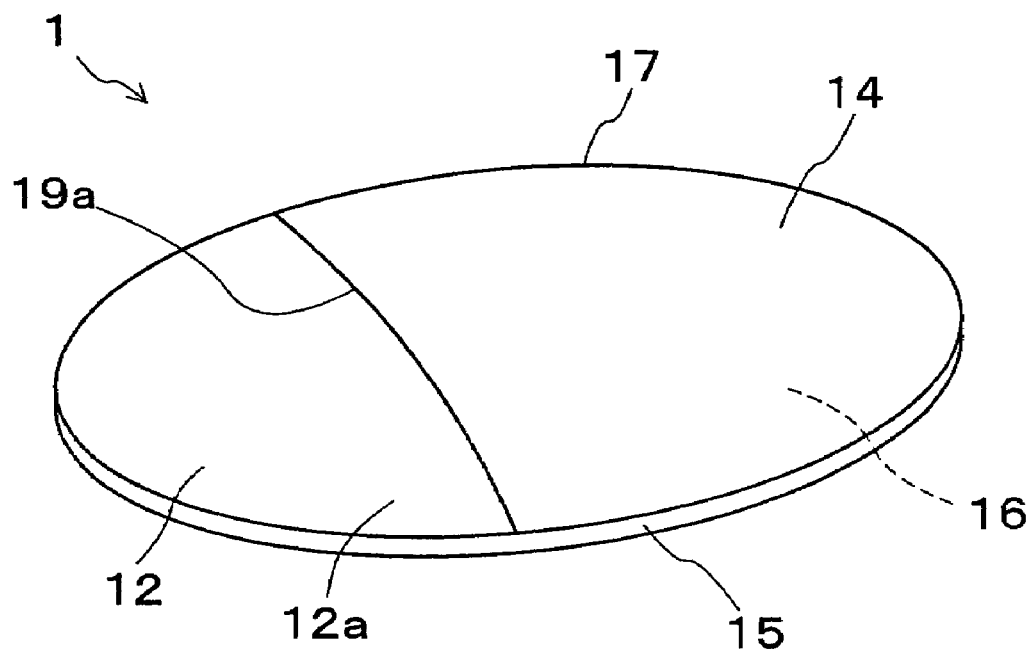
FIG. 3 shows a back (opposite side to the body side) of the interlabial pad of the first embodiment.
Figure 4:
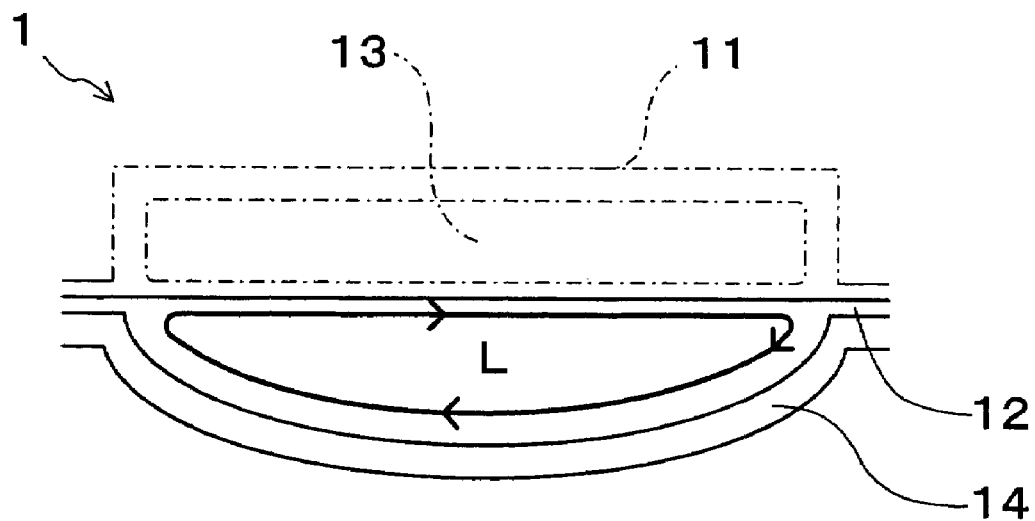
FIG. 4 is an illustrative drawing for illustrating the whole inner circumferential length of the finger insertion space of a mini-sheet attached to the interlabial pad of the first embodiment.

First, an interlabial pad where a pocket like mini-sheet is attached on the opposite side face to the body side shall be described. FIG. 1 shows inner components of an interlabial pad 1 of the first embodiment, FIG. 2 and FIG. 3 show the appearance of the interlabial pad 1 of the first embodiment, and FIG. 4 is a partial cross section in the lateral direction of the interlabial pad 1 where a part of the interlabial pad 1 is cut off for illustrating concretely the "whole inner circumferential length of the finger insertion opening".

<Basic Composition>

The interlabial pad 1 of this embodiment comprises, as shown in FIG. 1, an absorbent layer 2 having a surface side sheet 11 (body side) made of water permeable material, a back side sheet 12 (the opposite side face to the body side) made of non water permeable material and an absorbent body 13, and a mini-sheet 14 attached to the back side sheet 12.

The absorbent layer 2 is formed integrally by bonding the surface side sheet 11 and the back side sheet 12 at a periphery 15 so as to confine the absorbent body 13. The bonding of the surface side sheet 11 and the back side sheet 12 is compounded by heat seal and/or hot melt type adhesive. Besides, menstrual blood held by the absorbent body is prevented from leaking out of the interlabial pad 1, because the back side sheet 12 is made of a water impermeable material.

The mini-sheet 14 is attached to the absorbent layer 2, using pressure sensitive hot melt, heat sensitive hot melt or others as adhesive, and, it may be applied in a planar, linear, helical or dot form or the like.

As shown in FIG. 2, the surface side sheet 11 is disposed in the body side face of the interlabial pad 1 and comes to be flat.

On the other hand, as shown in FIG. 3, the back side sheet 12 is disposed in the opposite side face to the body side of the interlabial pad, and the mini-sheet 14 is bonded with this opposite side face to the body side 12a at an outer edge 17 except for a finger insertion opening 19a, so as to cover said back side sheet 12 on the order of approximately two thirds.

As obvious from this FIG. 3, according to this embodiment, a pocket 16 constituting a space for inserting a finger directing the ball of the finger (especially, fingerprint portion) to the back side sheet 12, only by binding the mini-sheet 14 having a longitudinal length shorter than the back side sheet 12 and a lateral direction equal to the same, with the back side sheet 12 at the outer edge 17 thereof. Consequently, it is unnecessary to pass through a specially complicated manufacturing process in order to make a finger insertion opening 19a, making possible to realize an interlabial pad 1 easy to wear, all the way avoiding the fall of the productivity.

It should be appreciated that the central dimension in the longitudinal direction of the absorbent layer is 85 mm, and the central dimension in the longitudinal direction of the mini-sheet 14 is around 55 mm. Therefore, the back side sheet 12 comes to have an area not covered with the mini-sheet 14 in a range of the order of 30 mm in the longitudinal direction.

The "whole inner circumferential length of the finger insertion opening" turning to be the magnitude of the finger insertion opening 19a is a length shown by "L" in FIG. 4, and in FIG. 4, portions unnecessary for describing the length of the "whole inner circumferential length of the finger insertion opening" are shown by alternate short and long dash lines. In this embodiment, the length of this "L" is on the order of 40 mm.

<Mini-Sheet Bonding Position>

Figure 5:
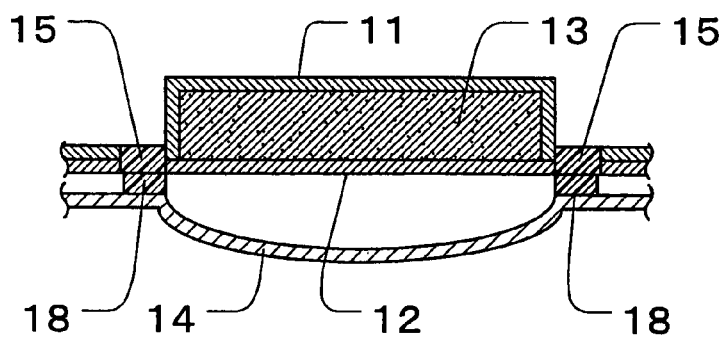
FIGS. 5A-D illustrate the attachment position of the mini-sheet of the interlabial pad of the first embodiment.
Figure 5:
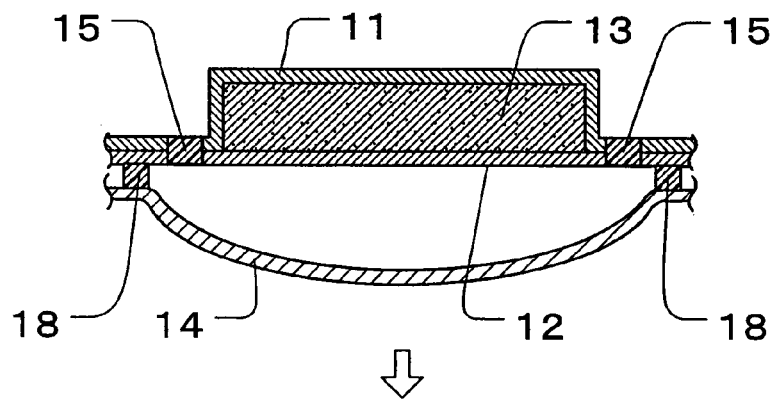
Figure 5:
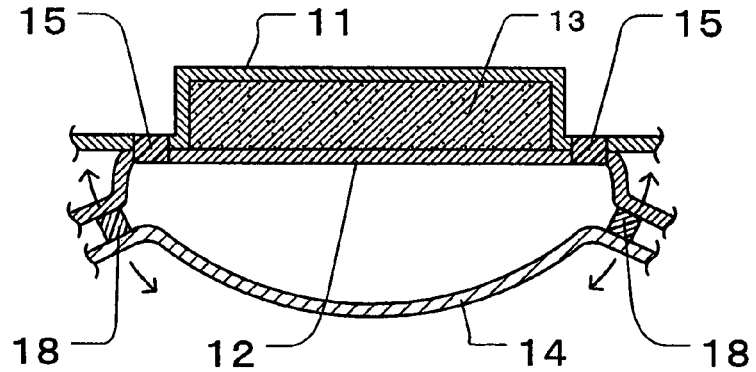
Figure 5:
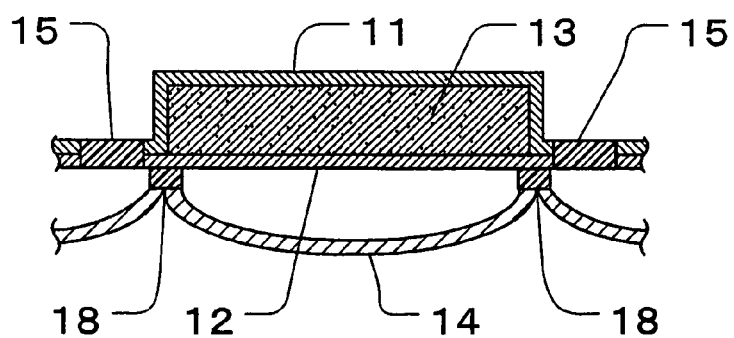

Next, the bonding position of the mini-sheet in respect to the absorbent layer shall be described. FIG. 5 is a longitudinal cross section showing a cross section in the lateral direction of an interlabial pad in order to illustrate the bonding state of the mini-sheet 14.

As shown in FIG. 5(A), in case of positioning a bonding portion 18 of the mini-sheet 14 and the back side sheet 12 at the same position as a periphery 15 which is a bonding point of the surface side sheet 11 and the back side sheet 12 and fixing them together, the portion of the periphery 15 ends up to harden, deteriorating the wear feeling of the interlabial pad. Concerning this, it can be avoided by fixing the mini-sheet 14 by arranging the bonding portion 18 elsewhere than the portion of the periphery 15.

However, as shown in FIG. 5(B), in case of positioning the bonding portion more outside than the portion of the periphery 15, it is conceived that a friction is generated by the movement of the bonding portion 18 according to the movement of the wearer, as shown in FIG. 5(C) and there is some possibility of stimulating the wearer.

In view of these facts, in practice, it is preferable to offset the periphery 15 and the bonding portion 18, and moreover, disposed the bonding portion 18 inside the portion of the periphery 15 as shown in FIG. 5(D).

<Use State>

Figure 6:
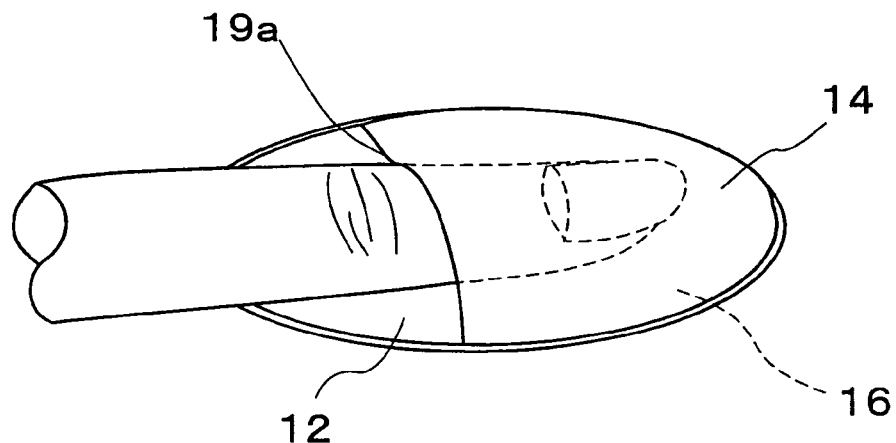
FIGS. 6A-C shows a state where a finger is inserted into a pocket for finger insertion disposed on the interlabial pad of the first embodiment.
Figure 6:
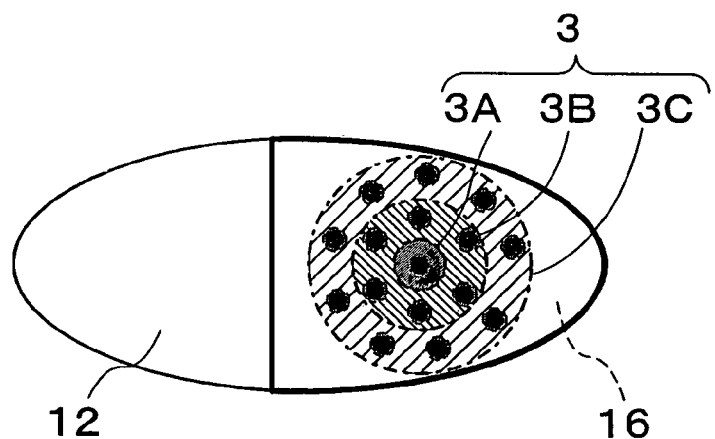
Figure 6:
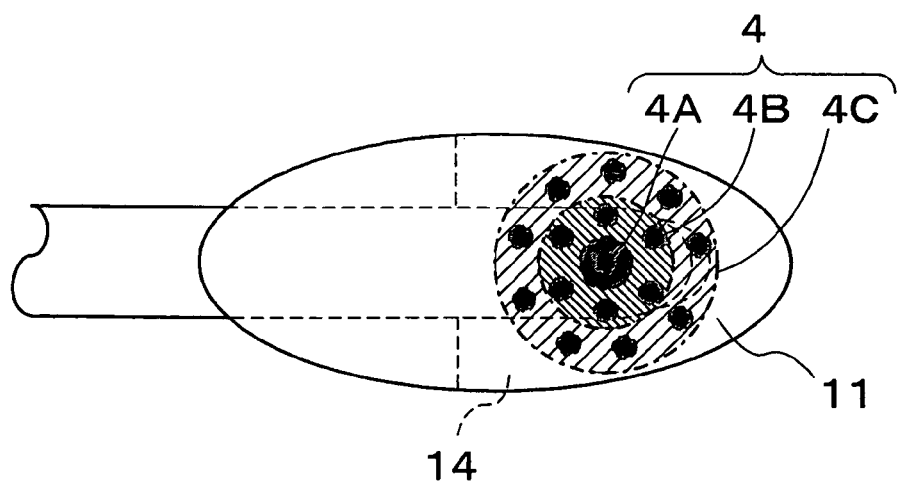
Figure 7:
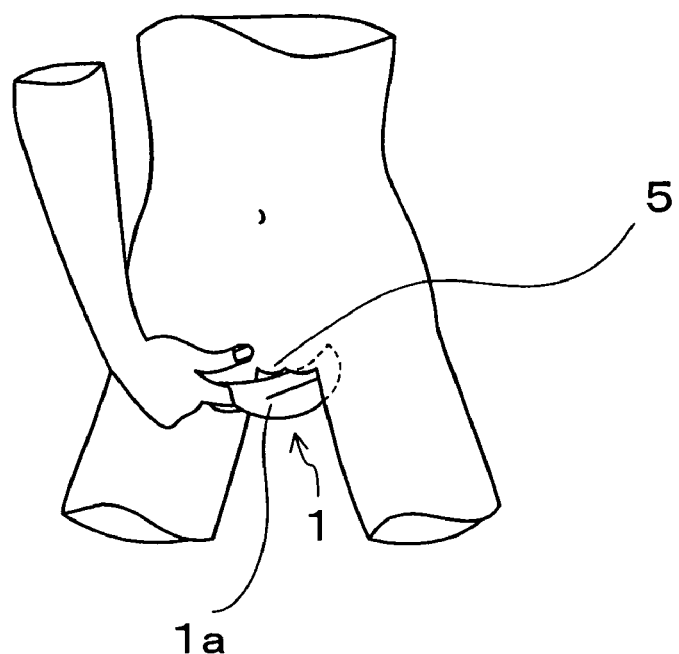
FIG. 7 shows a state of wearing the interlabial pad of the first embodiment between the labia.

Next, the used state of the interlabial pad 1 shall be described. FIG. 6 shows a state where the interlabial pad 1 is held on the fingertip, while FIG. 7 represents a state where the interlabial pad 1 is worn in the labia 5.

On the opposite side face to the body side of the interlabial pad 1, the wearer can insert her finger into a pocket 16 formed of a back side sheet 12 and a mini-sheet 14 from a finger insertion opening 19a constituting the opening of the pocket 16 by making the fingerprint face side in the vicinity of the first joint of the finger (vicinity of the terminal joint of the finger) in contact with the opposite side face to the body side 12a of the back side sheet 12. Thereby, the interlabial pad 1 can be held by the fingertip as shown in FIG. 6(A).

In case of inserting a finger in the pocket 16 in this way, a finger application point corresponding to the application point allowing to feel for easily the ostium vaginae situated deep in the labia exists at the point of contact with the fingerprint face of the finger. This finger application point corresponds to points includes in three areas shown in FIG. 6(B).

The area 3 containing the finger application point comprises an area 3A where finger application points most appropriate for feeling for the ostium vaginae exist, an area 3B where finger application points appropriate for feeling for the ostium vaginae exist, and an area 3C where finger application points acceptable for feeling for the ostium vaginae exist.

There, the finger insertion opening 19a directs the inserted finger so that the fingerprint face comes to the area 3 where such finger application points exist. Consequently, in case of inserting a finger from the finger insertion opening 19a into the pocket 16, as shown in FIG. 6(C), the fingerprint face of the finger turns to be positioned at the place corresponding to an area 4 where the application point exists on the body side face of the absorbent layer 2.

Consequently, as shown in FIG. 7, when the interlabial pad 1 is guided to the labia 5, it becomes possible to direct the interlabial pad 1 exactly to an appropriated position in the concave labia 5, by feeling the concave and convex of the labia 5 through the absorbent layer 2 with the ball of the first joint of the finger inserted into the pocket 16, making the labia 5 in contact with a (not shown) application point existing in the body side face 1a of the interlabial pad 1. It should be appreciated that, said area 4 also comprises an area 4A where application points most appropriate for feeling for the ostium vaginae exist, an area 4B where application points appropriate for feeling for the ostium vaginae exist, and an area 4C where application points acceptable for feeling for the ostium vaginae exist.

Figure 8:
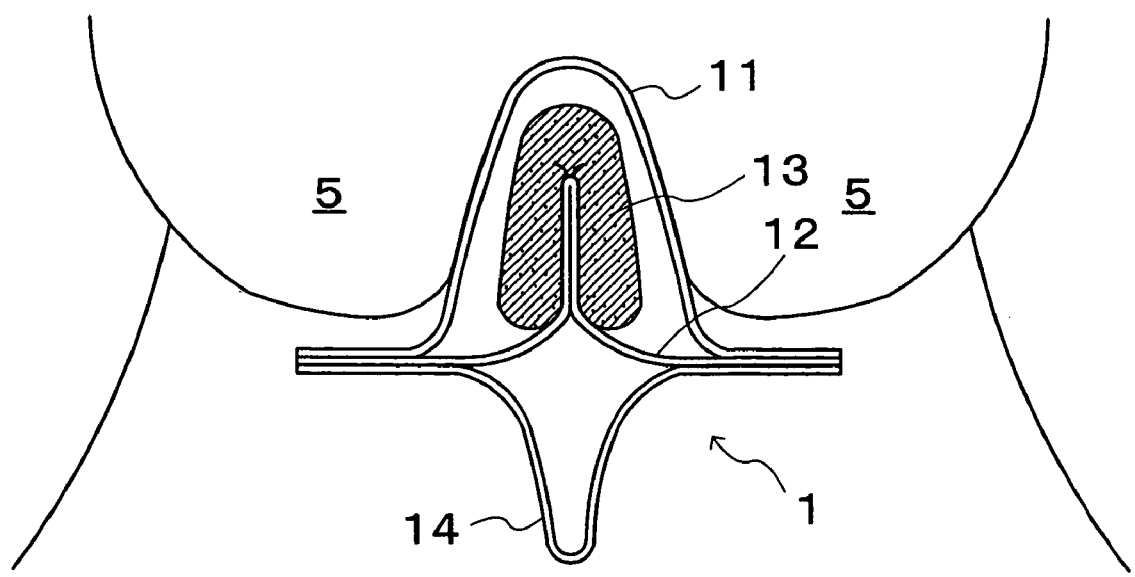
FIG. 8 shows a state of the mini-sheet after wearing the interlabial pad of the first embodiment.
Figure 9:
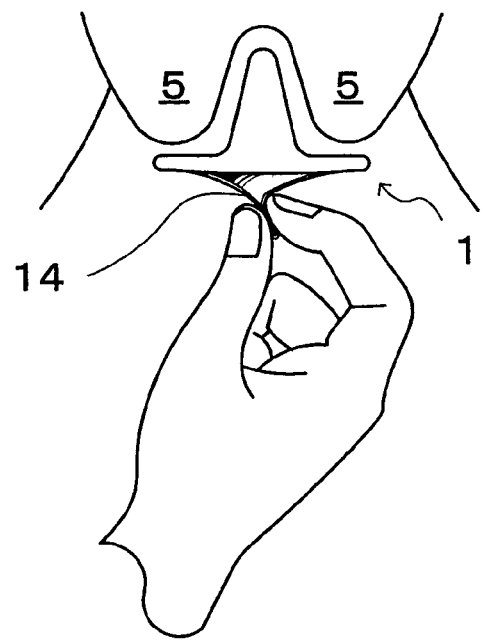
FIG. 9 shows a state of pulling extraction of the mini-sheet of the interlabial pad of the first embodiment.

Once the interlabial pad 1 fitted to the labia 5 and the finger is withdrawn from the pocket 16, the mini-sheet 14 slacks in a direction opposite to the body side as shown in FIG. 8. Therefore, when a used interlabial pad 1 is to be removed, as shown in FIG. 9, it is possible to pinch and pull the mini-sheet 14. It should be appreciated that, if the mini-sheet 14 is made of liquid impermeable material or moisture permeable material, the wearer can take off the interlabial pad 1 without soiling the fingers, even when she pinches the mini-sheet 14.

<Other Embodiments of Mini-Sheet>

Figure 10:
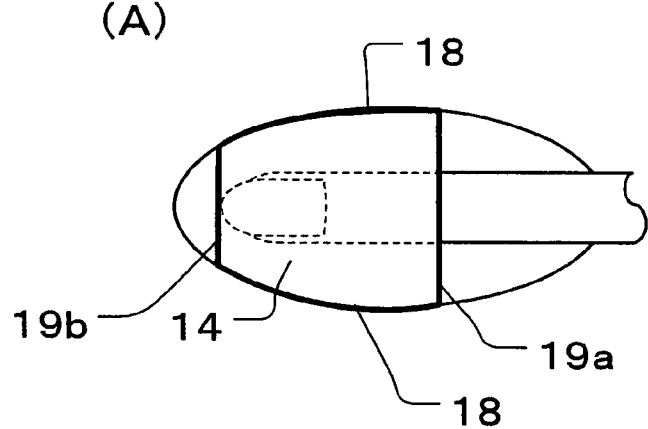
FIGS. 10A-B shows an interlabial pad to which a mini-sheet is attached to have two non-bonded portions.
Figure 10:
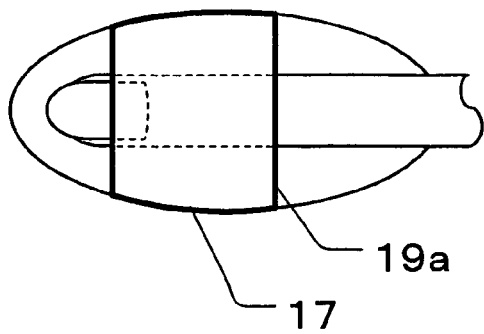
Figure 11:
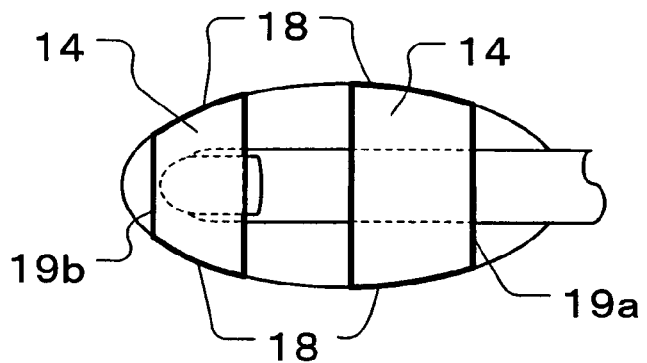
FIG. 11 shows the position of non-bonded portions in the back side sheet in case where a plurality of mini-sheets are attached.
Figure 12:
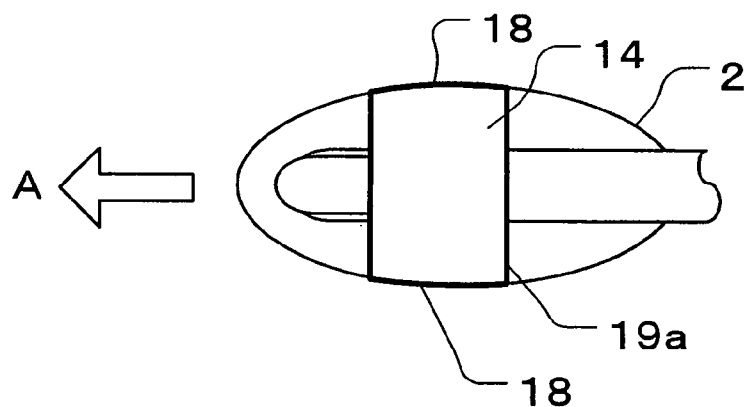
FIG. 12 shows a state where the mini-sheet attached to an interlabial pad has a length in a range equal or superior to 10% in the longitudinal direction.
Figure 13:
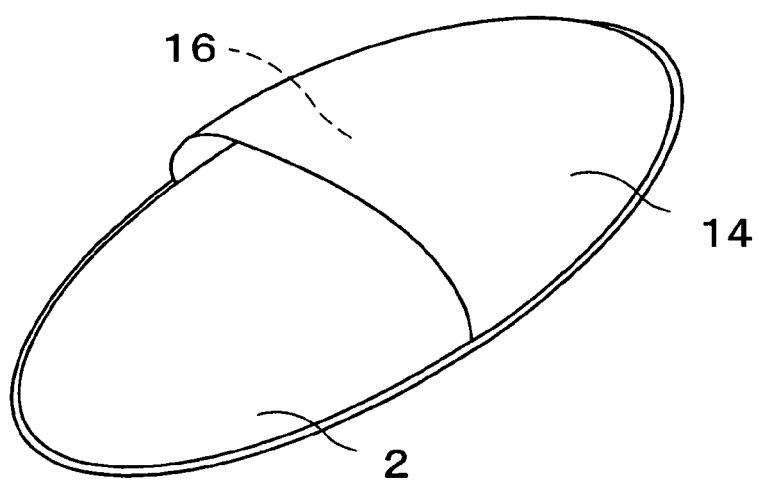
FIG. 13 shows an interlabial pad having a mini-sheet having a width larger than the absorbent layer of the interlabial pad.
Figure 14:
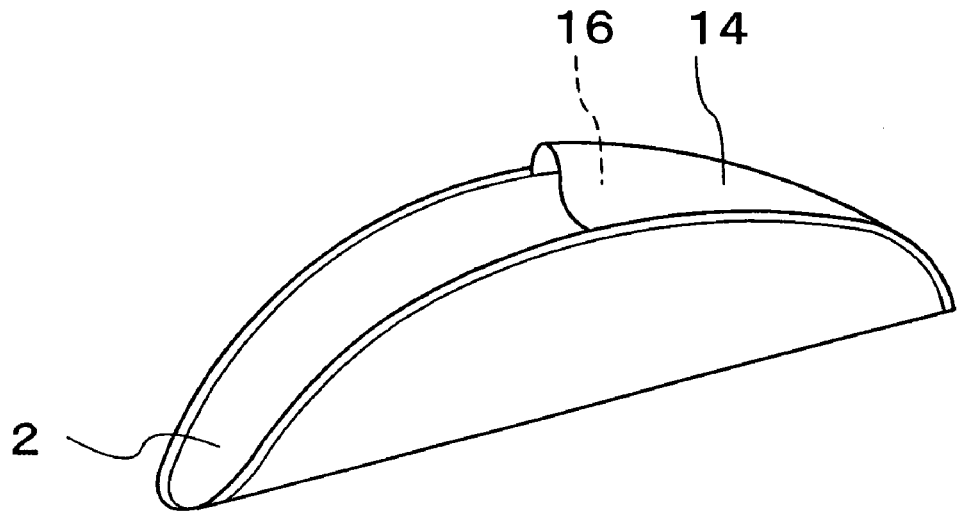
FIG. 14 shows an interlabial pad having a mini-sheet having a width smaller than the absorbent layer.
Figure 15:
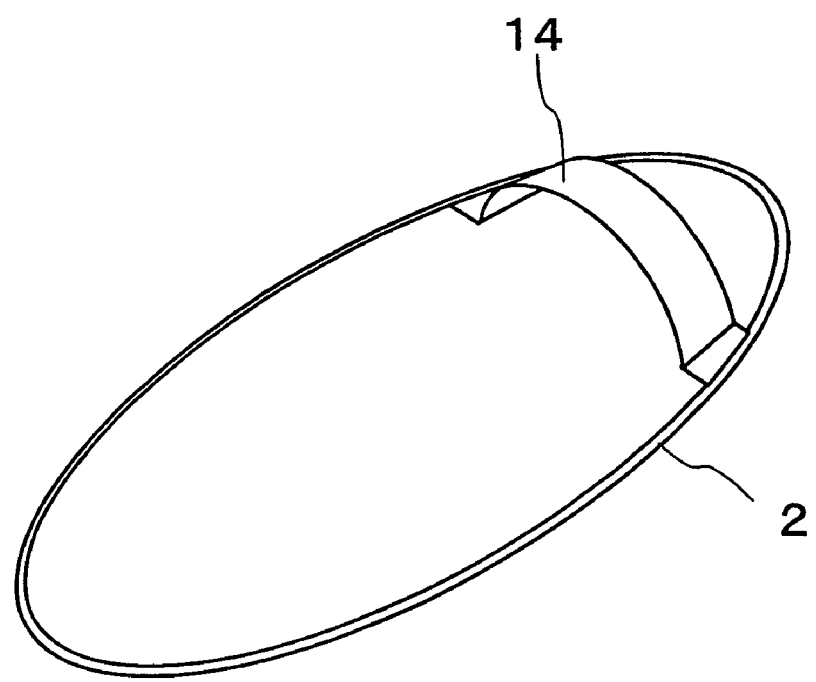
FIG. 15 shows an interlabial pad having a mini-sheet attached in a bridge shape.

Now, the other embodiments of mini-sheet will be described. FIG. 10 shows a state where a mini-sheet 14 is attached to have two non-bonded portions; FIG. 11 shows an interlabial pad where a plurality of mini-sheets 14 are attached; FIG. 12 shows the magnitude of the mini-sheet; FIG. 13 shows an interlabial pad having a mini-sheet 14 having a width in the lateral direction larger than the width of the absorbent layer 2; FIG. 14 shows an interlabial pad having a mini-sheet 14 having a width in the lateral direction smaller than the width of the absorbent layer 2; and FIG. 15 shows an interlabial pad having a mini-sheet 14 attached in a bridge shape.

In the present invention, it is sufficient for the mini-sheet that one or more binding portion is formed at respective side portion of the longitudinal direction at the opposite side to the body side of the interlabial pad, one or more non-bonded portion in the lateral direction of the opposite side face to the body side, and a finger insertion opening at said one or more non-bonded portions.

Consequently, the non-bonding portion can be provided not only at the portion becoming the finger insertion opening 19a, as mentioned above, but also at other portions.

For instance, in case where a second non-bonded portion 19b, which turns to be a finger insertion opening, exists as shown in FIG. 10(A), the second non-bonded portion 19b is positioned in a way to cover the fingertip of the wearer at a point where the fingertip of a finger inserted from the non-bonding portion 19a, which turns to be the finger insertion opening, is covered with the mini-sheet 14. By doing as this, a situation where the fingertip is exposed as shown in FIG. 10(B); attachment of menstrual blood or other problems may be avoided; and it is hygienic.

Moreover, as shown in FIG. 11, in case that a plurality of mini-sheets 14 are attached and that a plurality of non-bonding portions exist, the fingertip may not be exposed in the same manner if the second non-bonded portion 19b is provided at the most end.

As shown in FIG. 12, the length of the mini-sheet 14 is preferable made to have a length of a range of 10% or more in the longitudinal direction in respect to the absorbent layer 2. Thereby, it can be made obvious that the finger insertion direction is the direction of A. In this sense, a "length of 10% or more of the mini-sheet 14" plays a role of suggesting the finger insertion direction, in the interlabial pad according to the present invention.

It should be appreciated that, in case there are a plurality of mini-sheets, the range from the non-bonded portion to turn to be the finger insertion opening to the non-bonding portion at the most end (for instance, from the finger insertion opening 19a to the second non-bonded portion 19b as shown in FIG. 11) may be equal or superior to 10% of the mini-sheet.

As the other embodiments concerning the mini-sheet 14, as shown in FIG. 13, an embodiment where the width in the lateral direction of the mini-sheet 14 is made lager than the width of the absorbent layer 2 to cope with a user having relatively large fingers may be referred to. Also, as shown in FIG. 14, it is possible to realize an embodiment where the width in the lateral direction of the mini-sheet 14 is made smaller than the width of the absorbent layer 2 to cope with a user having thin fingers. It should be appreciated that, in case of FIG. 14, it is possible to increase the number of target users, by making the mini-sheet 14 distensible or elastically stretchable. As still another example, as shown in FIG. 15, by making the mini-sheet 14 in bridge form the quantity of material used for the mini-sheet 14 may be reduced so that the cost is reduced, too.

[Use with Sanitary Napkin]

Figure 16:
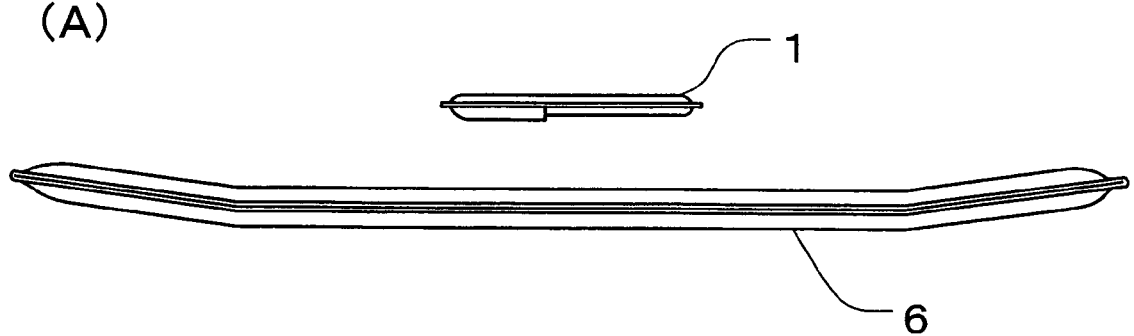
FIGS. 16A-B shows a state where the interlabial pad of the first embodiment is used at the same time with a sanitary napkin.
Figure 16:
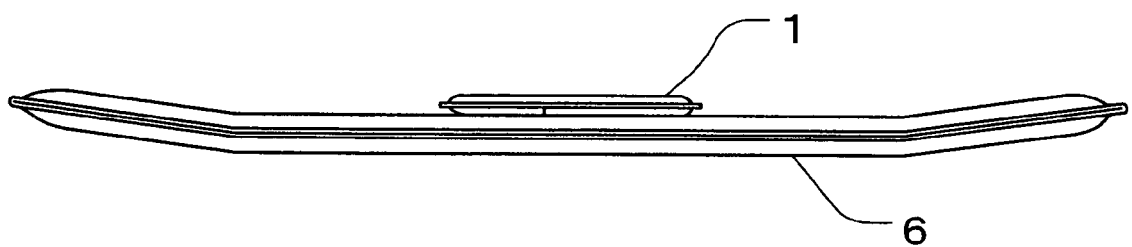

The interlabial pad 1 according to the present invention may be used together with an ordinary sanitary napkin 6, as shown in FIG. 16. As a wearing method, the interlabial pad 1 is worn in between the labia and the sanitary napkin 6 is worn on the underwear. By doing like this, the interlabial pad 1 can be used effectively even the day of abundant menstrual blood.

Second Embodiment

Figure 17:
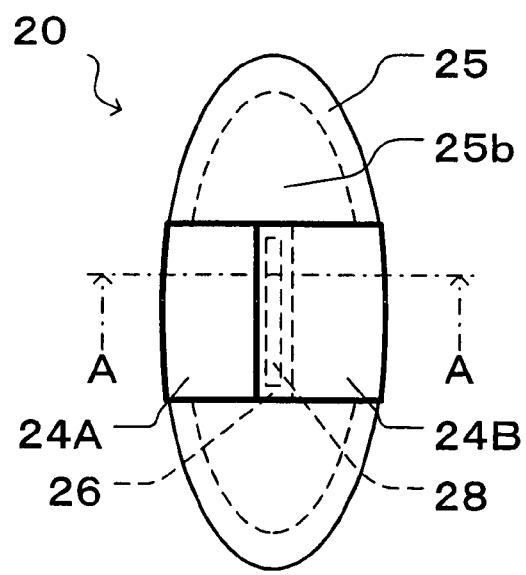
FIG. 17 shows the opposite side face to the body side of an interlabial pad with a flap portion of a second embodiment.
Figure 18:
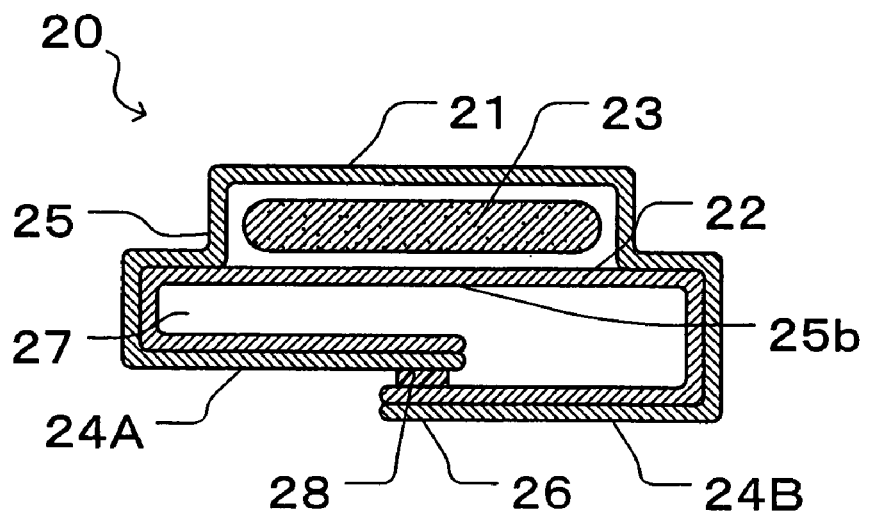
FIG. 18 shows a cross section along A-A of FIG. 17.
Figure 19:
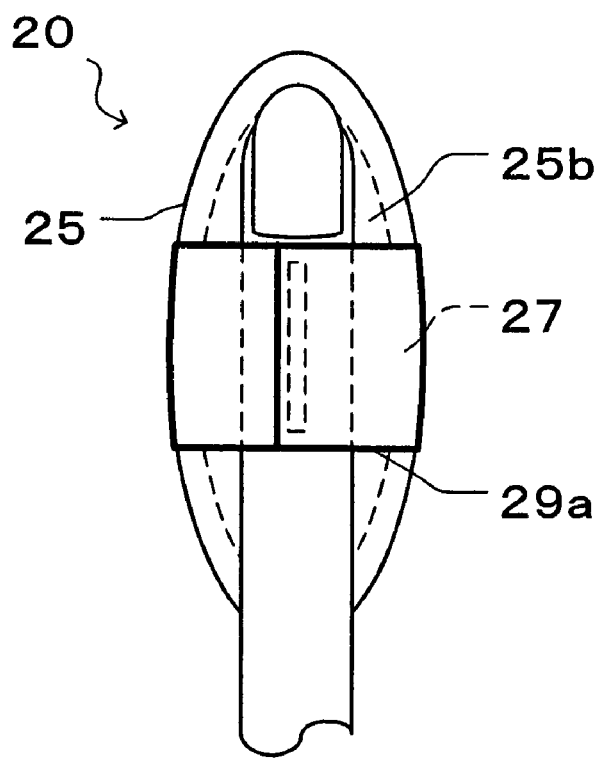
FIG. 19 shows a state where the interlabial pad with a flap section of the second embodiment is fitted on the fingertip.
Figure 20:
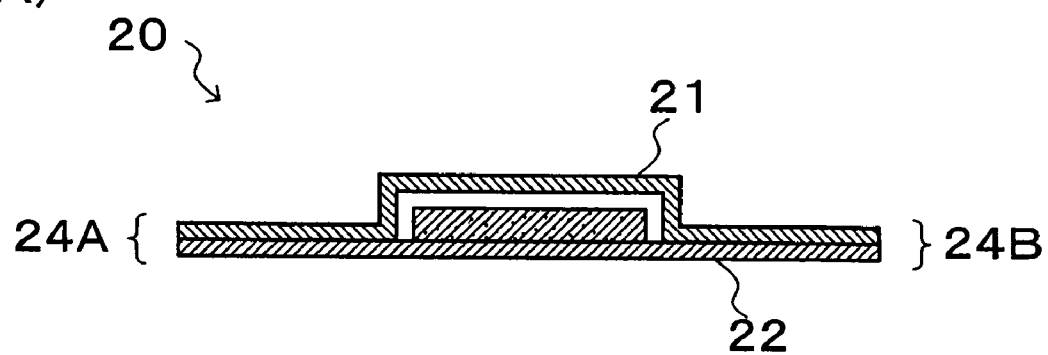
FIGS. 20A-C shows a composition of the flap section of the interlabial pad with the flap section of the second embodiment is fitted on the fingertip.
Figure 20:
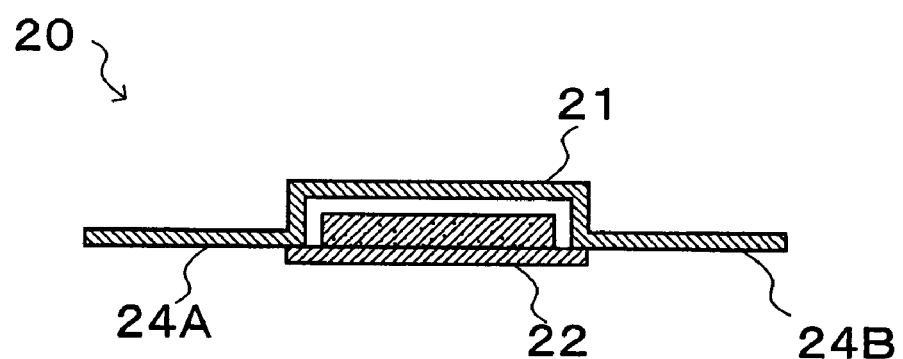
Figure 20:
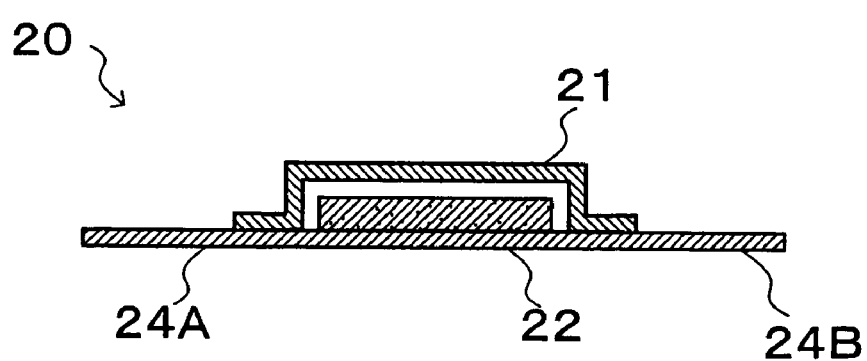
Figure 21:
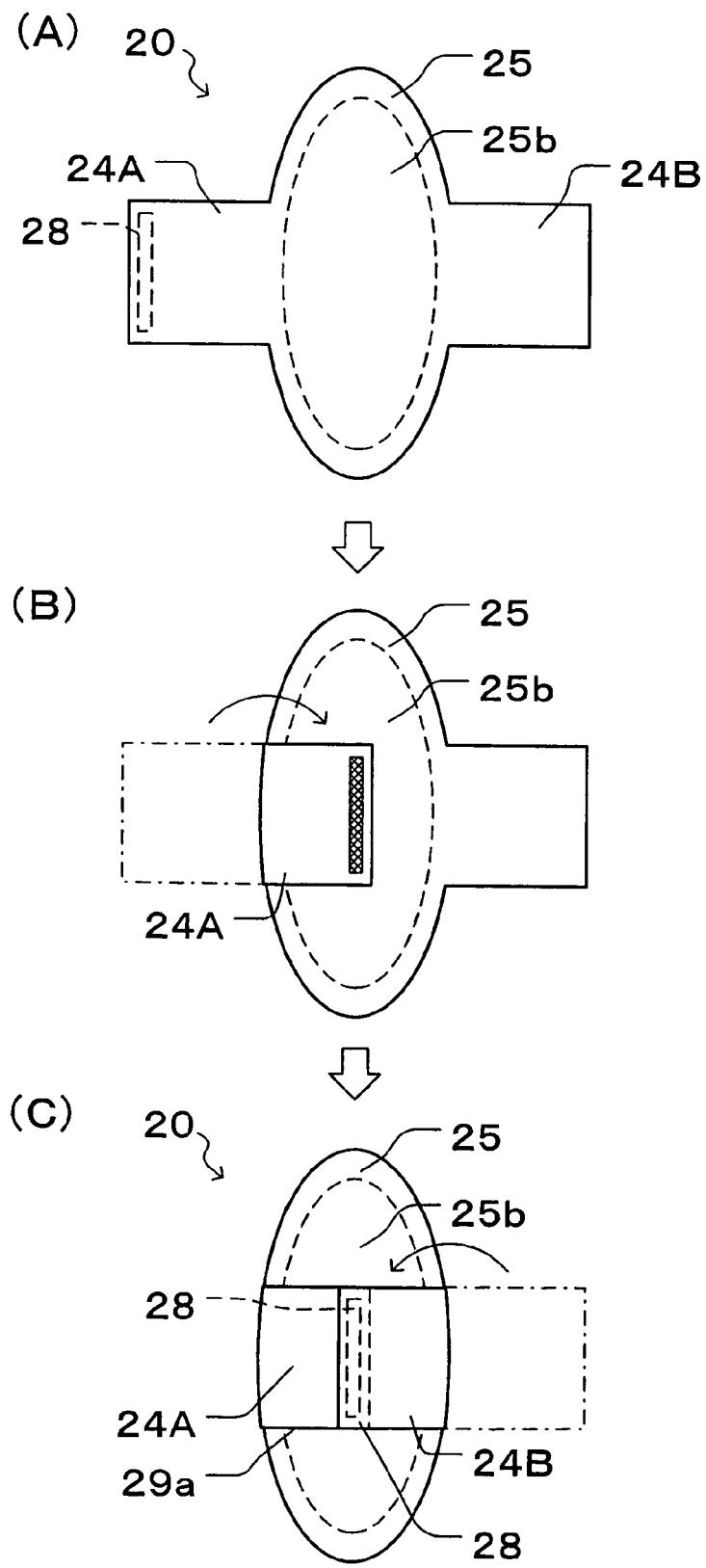
FIGS. 21A-C represent a process diagram showing steps for forming the finger insertion opening by bonding each terminal section of a pair of flap sections of the interlabial pad with the flap sections of the second embodiment.

Now, an interlabial pad with flap a portion shall be described. FIG. 17 shows the opposite side face to the body side of an interlabial pad 20 with flap portions 24A and 24B; FIG. 18 shows a cross section along A-A of FIG. 17; FIG. 19 shows a state where the interlabial pad 20 is fitted on the fingertip; FIG. 20 shows components of the flap portions 24A and 24B of the interlabial pad 20; and FIG. 21 is a process diagram showing steps for forming the finger insertion opening 29a by bonding the flap portions 24A and 24B each other.

As shown in FIG. 17, the absorbent layer 25 has a lateral dimension and a longitudinal dimension and is substantially longer in the longitudinal dimension. Then, flap portions 24A and 24B are provided at both side edges of this absorbent layer 25, these flap portions 24A and 24B are folded toward the opposite side face to the body side 25b of the absorbent layer 25, and a superposition portion 26 where both are superposed is adhered with an adhesive 28. It should be appreciated that this superposition portion 26 may be adhered by any means of adhesion, and in addition to the use of an adhesive as in this embodiment, heat seal or other methods may also be used.

As shown in FIG. 18, the absorbent layer 25 is composed by sandwiching an absorbent body 23 with a water permeable surface side sheet 21 and water impermeable back side sheet 22. Then, the surface side sheet 21 and back side sheet 22 are prolonged by a same dimension from both side edges of the absorbent layer 25, and the flap portion is formed in this prolonged portion. Then, a finger insertion space 27 is formed between the flap portions 24A and 24B where the superposition portion 26 is adhered, and the opposite side face to the body side 25b of the absorbent layer 25. Therefore, as shown in FIG. 19, the wearer can insert a finger from the finger insertion opening 29b into the finger insertion space 27 in contact with the opposite side face to the body side 25b of the absorbent layer 25.

Though the flap portions 24A and 24B are formed by prolonging the surface side sheet 21 and back side sheet 22 by a same dimension in this embodiment, as shown in FIG. 20(A), but only the surface side sheet 21 may be prolonged, as shown in FIG. 20(B), or only the back side sheet 22 may be prolonged, as shown in FIG. 20(C).

In order to form a finger insertion opening 29a, as shown in FIG. 21(A), first, adhesive 28 is applied to the body side face of the terminal portion of the flap portion 24A. Then, as shown in FIG. 21(B), the flap portion 24A is folded toward the opposite side face to the body side 25b of the absorbent layer 25. Next, as shown in FIG. 20(C), the flap portion 24B is also folded toward the opposite side face to the body side 25b of the absorbent layer 25. Then, the superposition portion 26 formed by superposing the terminal portion of the flap portion 24A and the terminal portion 24B is adhered with an adhesive. Whereby, a finger insertion opening 29a is formed.

<Other Shape of Absorbent Layer>

Figure 22:
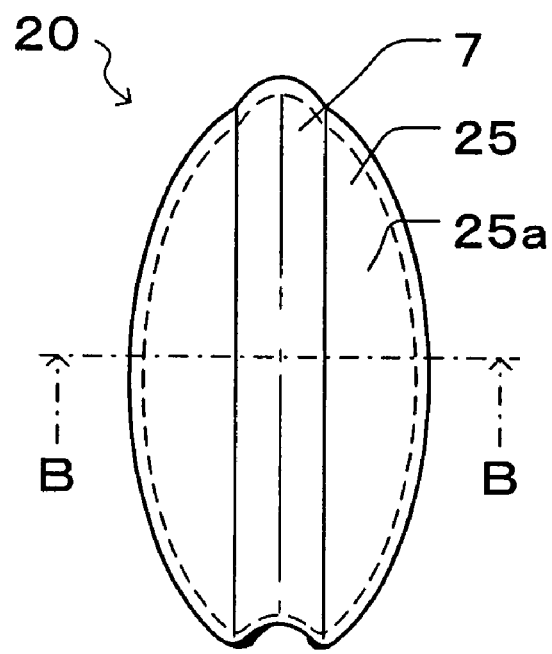
FIG. 22 shows a body side face of the interlabial pad with the flap sections of the second embodiment where an absorbent layer is folded.

Now, the other shape of the absorbent layer 25 in an interlabial pad 20 shall be described. FIG. 22 shows an absorbent layer 25 folded in a way to be convex toward the body side, and FIG. 23 shows a cross section along B-B of FIG. 22.

As shown in FIG. 22, the absorbent layer 25 of the interlabial pad 20 has a long convex area 7 to be convex toward the body side. As this long convex area 7 is formed by simply folding the absorbent layer 25, it can be deformed according to the labial shape of the wearer, and the wearer can stick the long convex area 7 in the labia, independently of the personal equation of the labial shape or others. Besides, as the long convex area 7 is deformable fittingly in response to the pressure during the wearing or the pinching force of the labia, the deformation follow-up ability against the wearing pressure or others turns to be enhanced.

Figure 23:
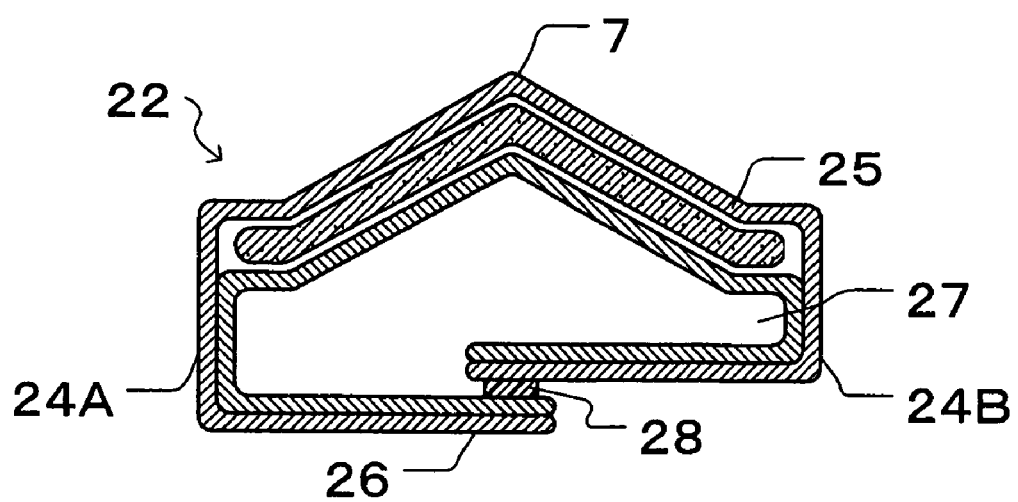
FIG. 23 shows a cross section along B-B of FIG. 22.

As shown in FIG. 23, the flap portions 24A and 24B prolonging from both side edges of the absorbent layer 25 are glued by an adhesive 28 at the superposition portion 26 where respective terminal portions are superposed and this adhesion is executed at a position allowing to control the extension of the absorbent layer 25. Therefore, the wearer can maintain the shape of the long convex area 7 until wearing the interlabial pad 20. In case of forming by folding the absorbent layer 25 of the long convex area 7, the adhesion of the flap portions 24A and 24B has simultaneously a function of forming the finger insertion opening 29a and, in addition, a function of preventing unnecessary deformation of the long convex area 7 by controlling the extension of the bent portion of the absorbent layer 25.

It should be appreciated that, as the upper side of a finger insertion space 27 (opposite side face to the body side 25b of absorbent layer 25) is inside the long convex area 7, the long convex area 7 turns to be able to be engaged deep in the labia, by wearing the interlabial pad 20 in a way to make the fingertip in contact with the opposite side face to the body side 25b of the absorbent layer 25.

<Other Union Form of Flap Portion>

Figure 24:
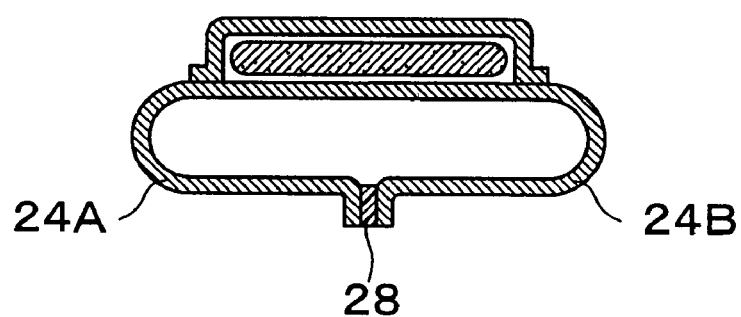
FIGS. 24A-B shows another bonding state of the flap sections and shows a state where the end of the pair of flap sections is folded and bonded.
Figure 24:
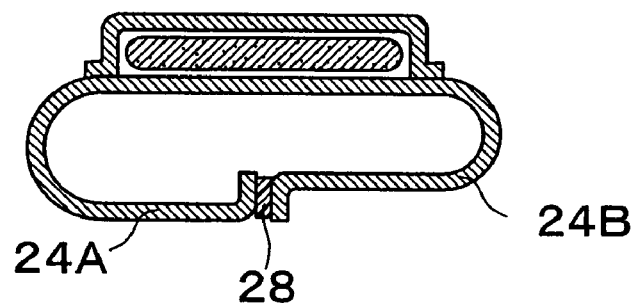
Figure 26:
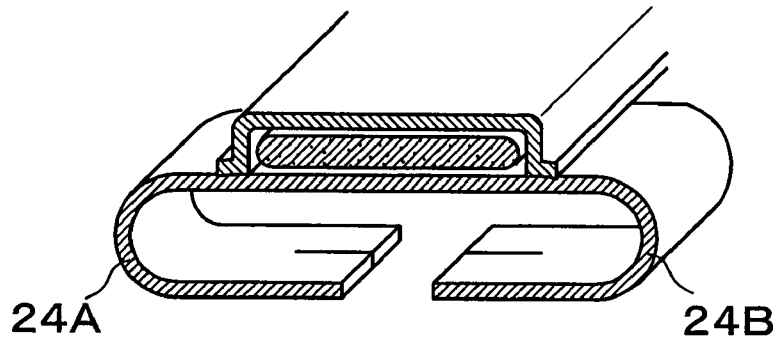
FIGS. 26A-C shows still another bonding state of the flap sections and shows a state where notches provided in the end of the pair of flap sections are engaged.
Figure 26:
Figure 26:
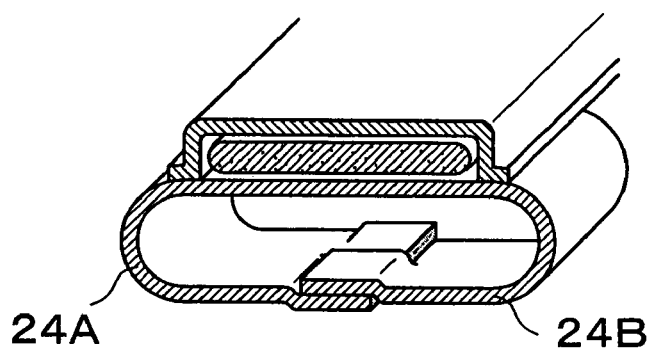
Figure 26:
Figure 26:
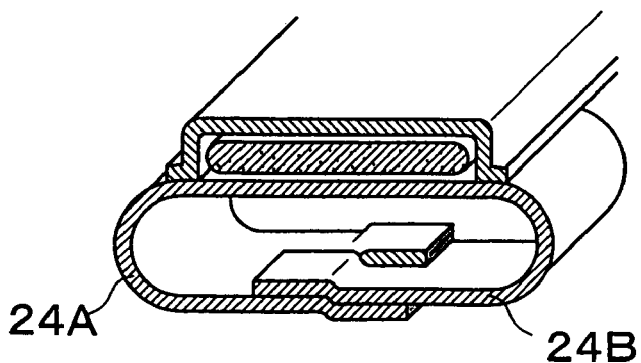
Figure 27:
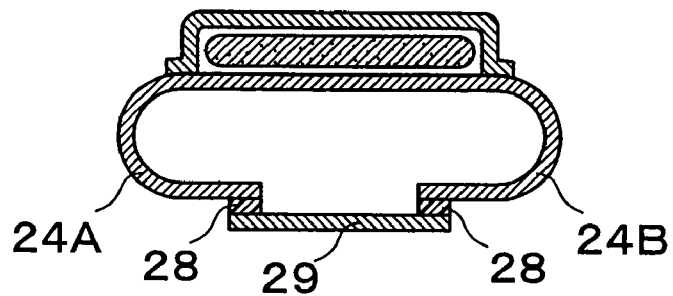
FIGS. 27A-B shows still another bonding state of the flap sections and shows a state where the pair of flap sections are linked using a linkage sheet.
Figure 27:
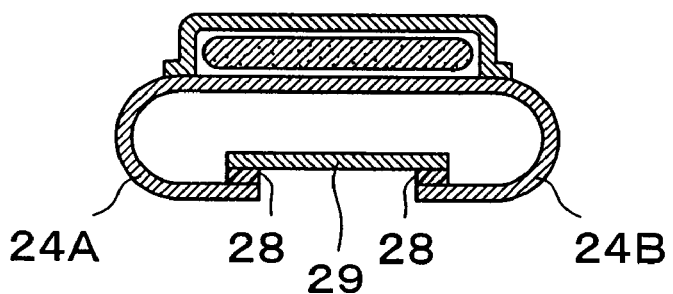
Figure 28:
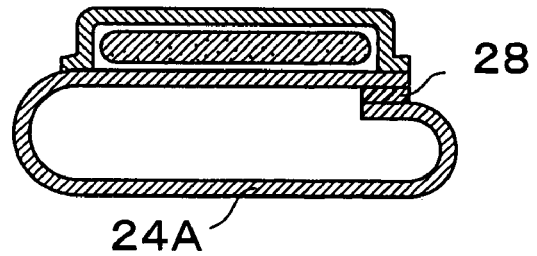
FIG. 28 shows another embodiment of a flap section and shows a state where the continuous flap section extending from the edge of one side of the absorbent layer is provided.

Now, another bonding form of the flap portion shall be described. FIG. 24 shows a state where terminal portions of the end of the flap portions 24A and 24B are folded face to face and affixed each other, FIG. 25 shows a state where terminals of the pair of flap portions 24A and 24B are folded and engaged, FIG. 26 shows a state where terminal portions the pair of flap portions 24A and 24B are notched and both are engaged, FIG. 27 shows a state where the pair of flap portions 24A and 24B are linked using a linkage sheet, and FIG. 28 shows a state where the back side sheet 22 extends from one side edge of the absorbent layer 25.

As mentioned above, it is possible to stick the terminal portions of the flap portions 24A and 24B face by butting them, and not superposing each other. For instance, as shown in FIG. 24(A), both terminal portions of flap portions 24A and 24B may be folded to the opposite side to the body side and the folded portion may be affixed with adhesive or, as shown in FIG. 24(B), terminal portions may be bent in different directions, to be more specific, the terminal of 24 may be bent upward and the terminal of 24B downward, and the folded portion may be affixed with adhesive 28.

Figure 25:
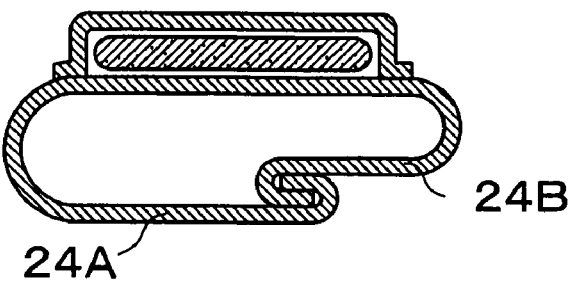
FIG. 25 shows another bonding state of the flap sections and shows a state where the end of the pair of flap sections is folded and engaged.

Also, as shown in FIG. 25, the terminal portion of the flap portion 24A may be folded toward the body side, the terminal portion of the flap portion 24B may be folded toward the opposite side to the body side, and the flap portion 24A and the flap portion 24B may be combined in such a way to hook both terminal portions each other.

Otherwise, the terminal portion of the flap portion 24A and the terminal portion of the flap portion may be notched respectively by a same dimension as shown in FIG. 26(A), these notches are engaged as shown in FIG. 26(B), and the flap portion 24A and the flap portion 24B may be combined as shown in FIG. 26(C).

And, a linkage sheet 29 different from the flap portions 24A and 24B may separately be attached, and the flap portions 24A and 24B may be linked by the same. For instance, the flap portions 24A and 24B may be folded toward the opposite side to the body side of the absorbent layer 25 and, thereafter, as shown in FIG. 27(A), the linkage sheet 29 may be affixed under the flap portions 24A and 24B with the adhesive 28 for linking the both or, as shown in FIG. 27(B), the linkage sheet 29 may be affixed on the flap portions 24A and 24B with the adhesive 28 for linking the two.

Moreover, in place of providing the flap portion at both side edges of the absorbent layer 25, the flap portion 24 A may be composed by extending the back side sheet 22 only from one side of the absorbent layer 25, as shown in FIG. 28, and the same may be glued to the other side of the absorbent layer 25 with the adhesive 28.

Figure 29:
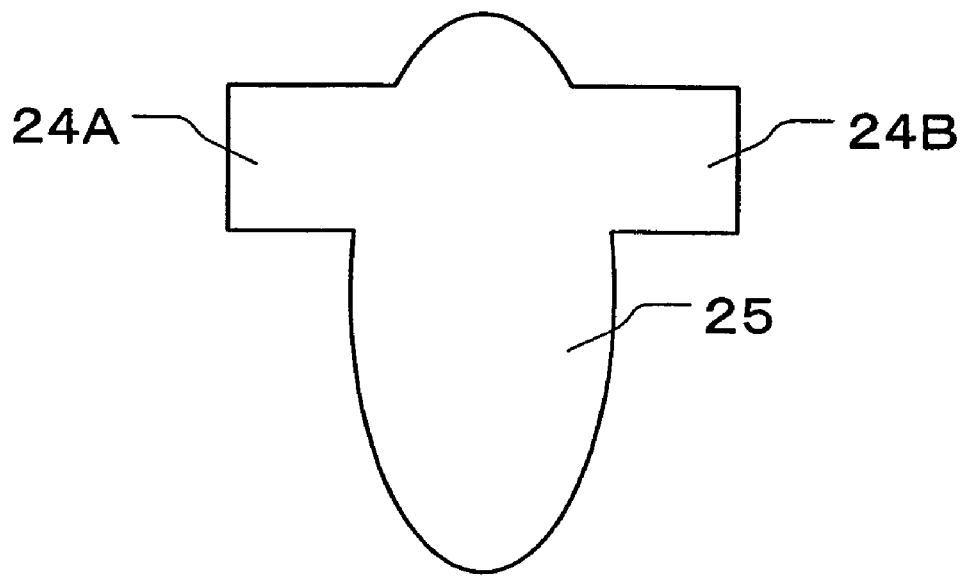
FIGS. 29A-B shows still another embodiment of flap sections and shows a state where the flap sections are provided near one end in the longitudinal direction of the interlabial pad.
Figure 29:
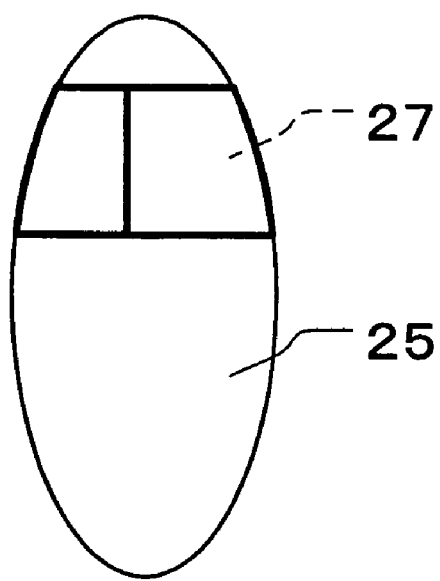

In addition to the arrangement of the flap portion in the middle zone of the absorbent layer 25 as mentioned above, the disposition thereof may be biased to one end in the longitudinal direction of the absorbent layer 25, as shown in FIG. 29(A). In this case, the tip of the finger inserted into the finger insertion space 27 is prevented to be exposed largely, because the finger insertion space 27 formed by sticking the flap portions 24A and 24B encloses the fingertip entirely, as shown in FIG. 29(B) when the wearer inserts the finger therein.

Figure 30:
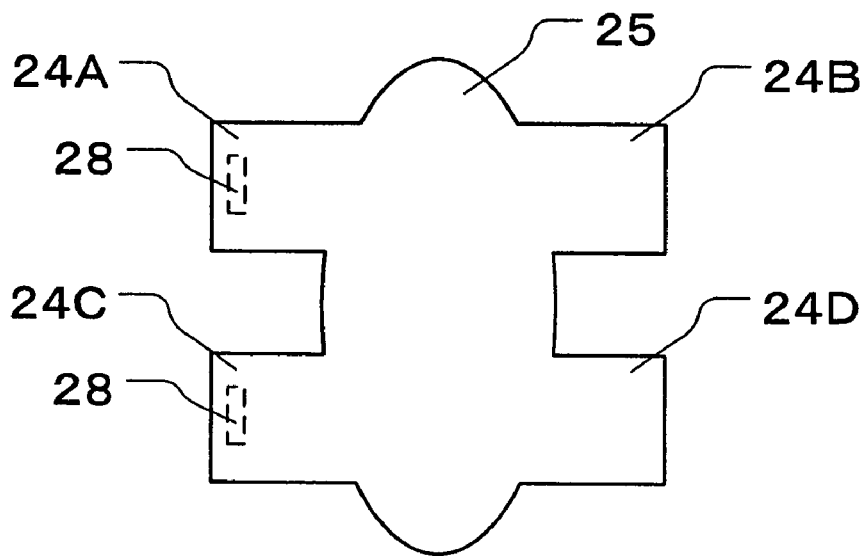
FIG. 30 is a plan view illustrating another type of flap portion of the interlabial pad, which has a plurality of flap portions.

Besides, in addition to the arrangement of flap portions one by one at both side edges, they may be disposed in plurality along each side edge, as shown in FIG. 30, by disposing for instance 24A and 24C along one side edge of the absorbent layer 25 and 24B and 24D along the other side edge, respectively.

Third Embodiment

Figure 31:
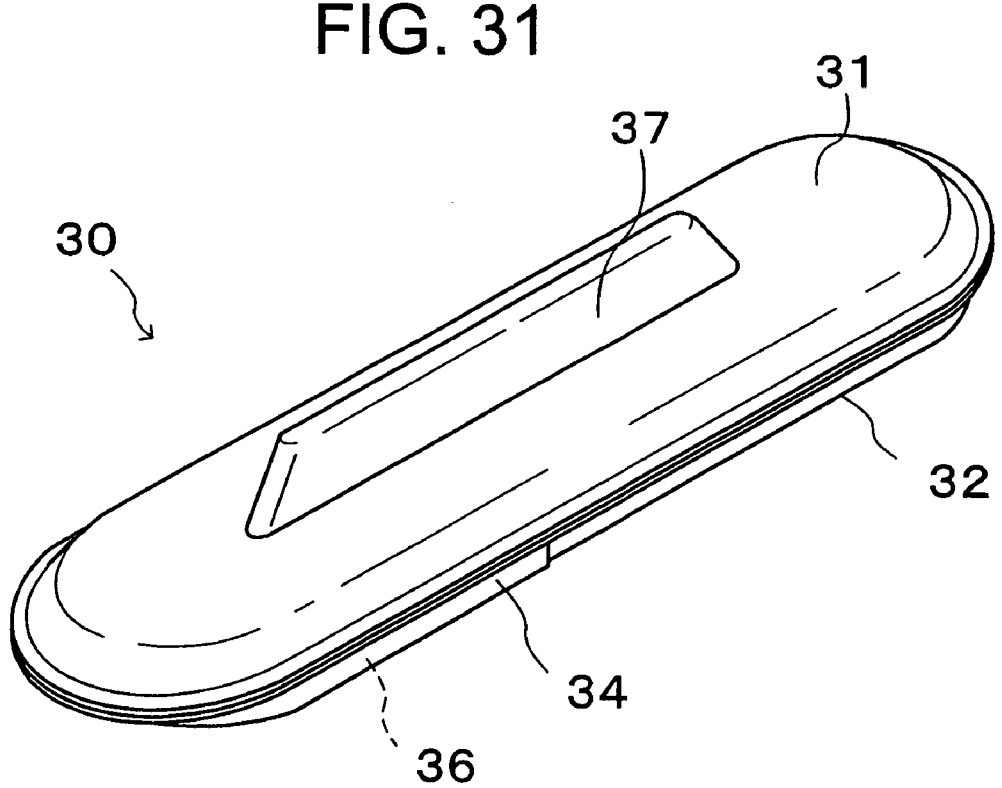
FIG. 31 is a perspective view of an interlabial pad having a long convex area of a third embodiment.

Next, an interlabial pad having a long convex area protruding toward the body side in the body side face shall be described. FIG. 31 is a perspective view of an interlabial pad 30 having a long convex area 37.

As shown in FIG. 31, the interlabial pad 30 has a long convex area 37 on a surface side sheet 31 disposed on the body side face thereof. Besides, a mini-sheet 34 is disposed on the opposite side face to the body side and the structure allows to insert a finger into a finger insertion pocket 36. Therefore, it becomes possible to locate exactly the position for introducing the long convex area 37 into the labia with the finger inserted into the pocket 36. Then, the adhesion between the interlabial pad 30 and the labia can further be enhanced, by introducing the long convex area 37 deep in the labia of the wearer, making possible to improve the advantage of the interlabial pad product, excellent adherence.

This long convex area 37 is of the order of 30 mm in the longitudinal direction and of the order of 10 mm in height in the present embodiment; however, any dimension penetrating into the labia will do, independently of this dimension.

[Application of Pressure-Sensitive Adhesive]

For the interlabial pad of the present invention, pressure-sensitive adhesive may have been applied to a part of the body side face, in order to enhance the adherence with the body during the wearing.

In the present invention, as usable pressure-sensitive adhesive, a gel pressure-sensitive adhesive comprising water-soluble polymer, crosslinker, plasticizer and water, or others can be cited. More concretely, gelatin, polyacrylic sodium, polyvinyl alcohol, carboxyl methyl cellulose or others can be cited as example of water-soluble polymer, calcium chloride, sulfuric magnesium or other water-soluble metallic salts as example of crosslinker, and glycerin, wax, paraffin or others as example of plasticizer.

In addition, a pressure-sensitive hot melt can be used as pressure-sensitive adhesive. Pressure-sensitive hot melt can be obtained by taking a synthetic rubber resin such as styrene-butadiene-styrene block copolymer (SBS), styrene-isoprene-styrene block copolymer (SIS), styrene-ethylene-butadiene-styrene block copolymer (SEBS), styrene-ethylene-propylene-styrene block copolymer (SEPS), or others as principal component, and melt blending there a tackifier such as terpene resin, chlorophoium resin and a plasticizer such as wax.

Moreover, silicone resin base pressure-sensitive adhesives can also be used. As silicone resin base pressure-sensitive adhesive, mixtures obtained by taking silicone resin, fluorine resin as principal component, and mixing a crosslinker such as platinum, molybdenum, antimony or others and a plasticizer such as ester base wax, glycerin, machine oil or others can be cited.

Thus, a variety of pressure-sensitive adhesives exist; however, considering the application stability, it is preferable to use a pressure-sensitive type hot melt. As pressure-sensitive type hot melts presenting a high application stability, those obtained by melt blending 15 to 25% of SEBS, 15 to 35% of plasticizer and 40 to 70% of tackifier can be cited. As for this pressure-sensitive type hot melt, anti-oxidant, anti-fluorescent or others may be added in a range of 0.1 to 1.0%.

It should be appreciated that, as for the pressure-sensitive adhesive, it is preferable to cover the portion of pressure-sensitive adhesive with a sheet where a tissue paper which is a generally available release paper coated with silicone resin or a sheet where a film coated with silicone resin. By doing so, it is possible to prevent pollution or release of the pressure-sensitive adhesive during the storage.

As for mode of disposition of pressure-sensitive adhesive, planar shape, dot shape, network shape, linear shape, or others can be cited. The application position of pressure-sensitive adhesive is not particularly limited provided that it allows to affix to the body; however, it is preferable to apply linearly to the vicinity of both side portions of the surface side sheet in a range of breadth dimension of the order of 1 to 5 mm, considering especially the presence of tricogenous portion in this side portion of the labia.

Figure 32:
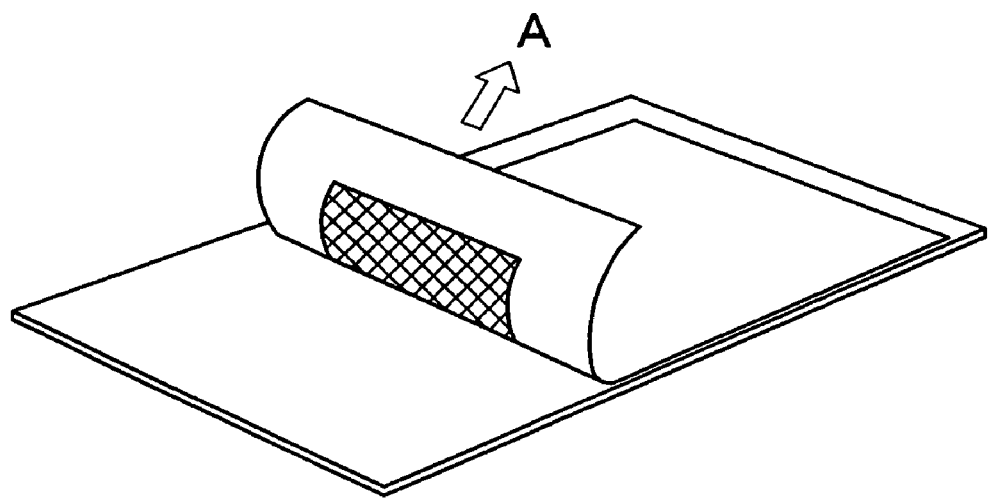
FIG. 32 is an illustrative drawing for illustrating a measurement method of peel strength of a pressure-sensitive adhesive, in the valuation method of adhesion of the pressure-sensitive adhesive applied to the body side face of the surface side sheet.
Figure 33:
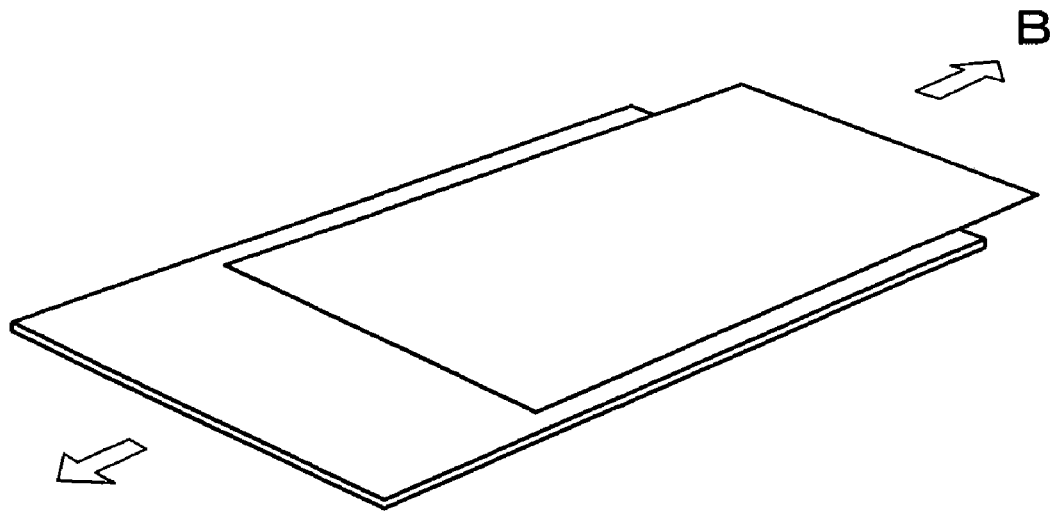
FIG. 33 is an illustrative drawing for illustrating a measurement method of shear strength of a pressure-sensitive adhesive, in the valuation method of adhesion of a pressure-sensitive adhesive applied to the body side face of the surface side sheet.

An example of valuation method of the cohesion of a pressure-sensitive adhesive shall be described. Such valuation method is devised to measure, the peel strength of the pressure-sensitive adhesive (refer to FIG. 32) and the shear strength of the pressure-sensitive adhesive (refer to FIG. 33), and performed using a constant speed elongation tensile testing machine and a stainless steel plate of 80 mm length-.times.50 mm width. For performing the valuation test, pressure-sensitive adhesive is applied previously 25 mm wide and 50 mm long on a polyethylene film of approximately same size as the stainless steel board and left for 30 min under the room temperature (20 degrees Celsius). Next, the polyethylene film is put lightly so that the pressure-sensitive adhesive comes into contact with the stainless steel board, and a roller of 2 kg is applied only one way. Thereafter, it is left for 0.30 min under the room temperature (20 degrees Celsius) to prepare a test piece. The portion of polyethylene film of the test piece prepared as mentioned above is pulled and peeled off in the direction of the arrow A shown in FIG. 32 for the peel strength test, and it is pulled in the direction of the arrow B shown in FIG. 33 for the shear strength test. Provided that, as test condition, the chuck interval (clamp interval) be set to 70 mm, and the tensile speed to 100 mm/min. It is preferable that the measured value of peel strength is 100 to 2000 mN/25 mm and the measured value of shear strength is 2900 to 15000 mN/25 mm in case of measuring according to the aforementioned method. These are considerations for the wearer's skin.

Moreover, the apparent length dimension in the lateral direction of the interlabial pad is preferably in a range of 10 to 60 mm and more preferably in a range of 20 to 40 mm. In case where the length dimension in the lateral direction is longer than 60 mm, the area not interposed between the labia rubs the femoral region or others of the wearer and there is some possibility that the friction generated by this exceeds the pinching force of the labia, and the interlabial pad falls down. On the other hand, in case where the length dimension in the lateral direction is shorter than 60 mm, the area that can be interposed between the labia reduces, and the contact area with the labial inner face reduces accordingly, and there is the possibility that the interlabial pad falls off.

Figure 34:
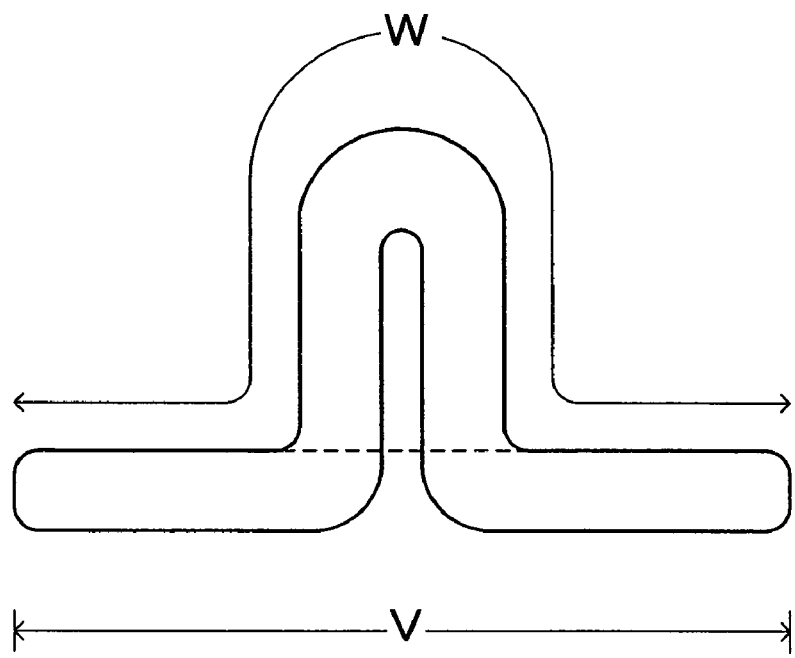
FIG. 34 is an illustrative drawing for illustrating the length dimension in the lateral direction of the interlabial pad.
Figure 35:
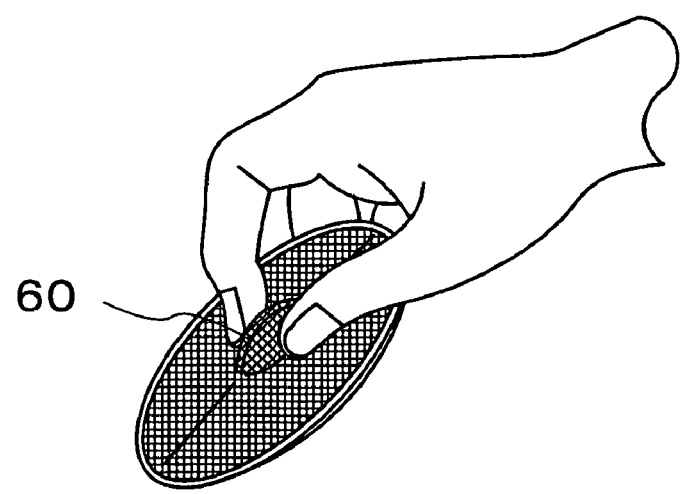
FIG. 35 illustrates a using state of an example of the prior art having a projection in the opposite side face to the body side of the interlabial pad.
Figure 36:
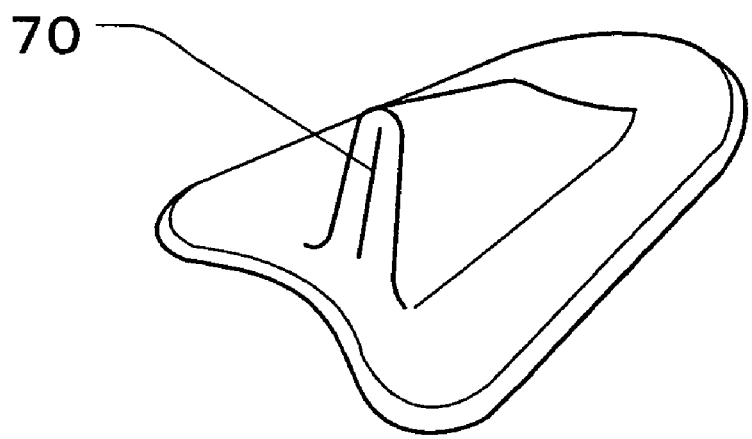
FIG. 36 shows a normal state of an example of incontinence prevention pad having a finger hole of the prior art.
Figure 37:
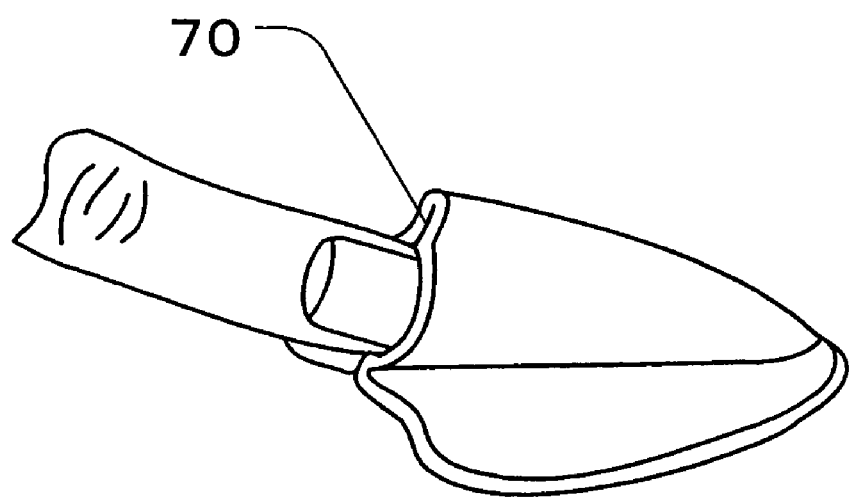
FIG. 37 shows a finger insertion state of the example of incontinence prevention pad having a finger hole of the prior art.

It should be appreciated that the aforementioned "apparent" means the distance between two points where the length dimension is shortest (corresponding to V in FIG. 34). This is defined deliberately, because in some cases, the contour between two points along the irregular shape, namely, the distance between two points in a flat state obtained by developing the irregular shape is treated as the actual length (corresponding to W in FIG. 34), in relation to the manufacturing process.

Moreover, in case where the longitudinal dimension of the interlabial pad is longer than 150 mm, the contact area between the opposite side face to the body side of the interlabial pad and the underwear or others becomes too large, and there is the possibility that a friction force bigger than the interlabial pad holding force of labia itself is generated, and the interlabial pad falls off from between the labia. On the other hand, if it is shorter than 60 mm, the interlabial pad can not secure an area sufficient to be engaged between the labia, and the interlabial pad falls off easily from between the labia. Consequently, the longitudinal length of the interlabial pad is preferably 60 to 150 mm, and more preferably 80 to 120 mm.

In case where the thickness of the interlabial pad is equal or superior to 20 mm, there is the possibility that the wearer has a foreign feeling during the wearing, because the interlabial pad is fitted to a sensitive area between the labia. On the other hand, if it is equal or inferior to 0.5 mm, the capacity of the contained absorbent body tends to becomes insufficient for absorbing menstrual blood, and there is the possibility that menstrual blood leaks out of the interlabial pad. Therefore, the thickness of the interlabial pad according to the present invention is preferably 0.5 to 20 mm, and more preferably, 2 to 10 mm.

[Shape of Interlabial Pad]

In the present invention, the shape of the interlabial pad may be any shape appropriate for the hold by pinching between the labia, and in addition to the elliptic shape as in the aforementioned embodiment, it may be oval, gourd-shape, drop-shape or others.

[Composition Material of Interlabial Pad]

<Water-Permeable Sheet>

Hydrophilic and non skin-irritating materials are used for the water-permeable sheet to be disposed on the body side of the interlabial pad. As such, non-woven fabric, sole or its combined material, obtained by the manufacturing methods such as melt blown, spun bond, point bond, through air, needle punch, wet spun lace, foam film or others, can be cited.

As fiber sheets, those sheets of sole or mixed fibers comprising solely or in combination component such as rayon, acetate, cotton, pulp or synthetic resin can be cited.

Among the materials, considering the liquid mobility from the inner face of the labia, chemical stimulation by an activator, and adhesion with the inner wall of the labia, it is preferable to laminate rayon with 1.1 to 4.4 dtex fineness and 7 to 51 mm fiber length by 40 to 80% of a total specific weight per unit area on the body surface side, and to laminate a mixture of rayon with 1.1 to 4.4 dtex fineness and 7 to 51 mm fiber length by 14 to 42% of a total specific weight per unit area and PET with 1.1 to 4.4 dtex fineness and 7 to 51 mm fiber length by 6 to 18% of a total specific weight per unit area on the clothing surface side. After laminating them so that the total specific weight per unit area of the two layers becomes 20 to 60 g/m.sup.2, the fibers are entangled by water-flow interlacing treatment and then dried to prepare spun lace nonwoven fabric with the thickness of 0.13 to 0.50 mm. The spun lace nonwoven prepared as described is preferable. At this time, by mixing PET on the clothing side, bulkiness can be easily maintained even if the permeable sheet becomes wet. Therefore, adhesion between the inner wall of the labia can be maintained.

<Absorbent Body>

Materials to be used for the absorbent body contained in the interlabial pad include pulp, chemical pulp, rayon, acetate, natural cotton, super absorbent polymer, fibrous super absorbent polymer, synthetic fiber and mixture thereof. A mixture blended as required is made into a sheet by technologies such as pressure bonding by embossing process, entanglement by needling that are well known in the art. The sheet may be adjusted by bulking, layering, folding, etc as required.

Materials for the sheet may be used in a sheet or powdered. Their types of usage are not particularly limited.

It is preferable for the absorbent body, although any material can be used as long as it is capable of absorbing and holding liquid (body fluid), to be bulky, hard-to-be deformed, less chemically stimulant, and highly flexible to fit into the labia. Specifically, a non woven sheet in which, 50 to 150 g/m.sup.2 of pulp selected from the range of the fiber length of 1 to 10 mm is laminated on the garment face side and, on the body face side, 150 to 250 g/m.sup.2 of a mixture obtained by mixing 60 to 90% of rayon with 1.1 to 4.4 dtex fineness and 20 to 51 mm fiber length with 40 to 10% of natural cotton by this mixing ratio is laminated, which then to be formed into a sheet by dotted embossing to have 2 to 10 mm bulkiness, and more preferable to have 3 to 5 mm bulkiness. Thereby, liquid can be easily transferred from the body face side to the garment face side resulting in the improvement of the absorbing and holding capacity. Furthermore, by providing a mesh spun lace non woven fabric of rayon with 1.1 to 4.4 dtex fineness and 25 to 51 mm fiber length by a specific weight per unit area of 15 to 40 g/m.sup.2, the liquid transferred from the body face side can be diffused by the mesh spun lace to be induced to almost all over the region of the pulp layer. Therefore, more liquid can be effectively absorbed.

In case of integrating the aforementioned absorbent body in the interlabial pad, it can be adjusted conveniently by regulating the volume, superposing, folding or others as necessary.

<Water Impermeable Sheet>

The material of water impermeable sheet used for the interlabial pad can be that which can prevent the menstrual blood kept in the absorbent body from a leak out of the interlabial pad. Furthermore the pad can be comprised of water vapor permeability material, thereby in wearing the pad, the sweat and the discomfort can be decreased.

As such material, for example, sheet form film where synthetic resin is made into a film, ventilation film obtained by filling with inorganic filler and treating through drawing, paper, laminate where non-woven fabric and film are combined, gas permeable liquid blocking sheet presenting 10 to 30% porosity and obtained by arranging capillary directed to an absorbent element side in a range of 0.1 to 0.6 mm, or others can be used.

Moreover, in case of considering a softness that would not deteriorate the wearing feeling, it is preferable to use for instance a film obtained in a specific weight per unit area of 15 to 30 g/m.sup.2 mainly composed of a low density polyethylene (LDPE) of a density of 0.900 to 0.925/cm.sup.3 in density. More preferably, the ratio contact may be reduced and the friction drag value may be lowered by installing convex upheavals through the emboss processing of the aforementioned film, in order to reduce the danger that the interlabial pad falls from the labia due to a high friction, when the water impermeable sheets come into contact with each other, a pad used at the same time, underwear or others, during the wearing between the labia.

<Mini-Sheet>

Material similar to the aforementioned water permeable sheet or water impermeable sheet may also be used, but it is preferable to use those stretchable or elastic at least in the lateral direction of the interlabial pad.

By using such material for mini-sheet, the interlabial pad according to the present invention can be used effectively independently of the fingertip size of the wearer, because the mini-sheet elongates at least in the breadth direction according to the size of the finger, even when the size of the fingertip of the wearer is larger than the set finger insertion opening.

Inherently elastic materials include, for example, synthetic rubbers resin such as styrene-butadiene-styrene block copolymer (SBS), styrene-isoprene-styrene block copolymer (SIS), urethane or others, film using amorphous olefin group resins selected from a density of 0.88 to 0.900 g/cm.sup.3 as raw material, porous foam film, net, or others. Also, fabric or textile where spinning filaments using synthetic rubber as raw material are knit in fabric may be used. Furthermore, spun bond non woven fabric, melt blown non woven fabric, expanded foam sheet mainly composed of synthetic rubber may also be used.

In consideration of soft texture during the wearing, as preferably, the porous foam film using SEBS as raw material, adjusted to a thickness of 15 to 40 micron, and composed in range of 0.28 to 1.77 mm.sup.2 in hole area and 40 to 70% in porosity can be cited.

As for non-woven fabric, spun lace non-woven fabrics using as raw material composite synthetic fibers such as heat shrinkable PE/PP, PE/PET, PP/PP or others wherein the core component is composed of a high melting component and the sleeve component a low melting component, and confounding fibers by water stream pressure, shrink type non-woven fabrics wherein fabric shrinkage is accelerated by applying the re-hot air processing, so-called stretchable wherein continuous long fibers are formed into a sheet by heat seal and, thereafter, submitted to a longitudinal coercive tentering, or others can be cited.

To be more specific, a shrink type non-woven fabric in a rage of 1.1 to 4.4 dtex in thickness, in a rage of 7 to 51 mm in length using as raw material composite synthetic fibers such as heat shrinkable PE/PP, PE/PET, PP/PP or others wherein the core component is composed of a high melting component, and adjusted in a specific weight per unit area of 10 to 60 g/m.sup.2 can be cited as soft and abundantly drapable preferable material. Furthermore, laminate materials of the aforementioned materials may also be used.

In case of using an inextensional material by affording extensionality, as for non-woven fabric, not only a bulky through air non-woven fabric using composite synthetic fibers such as heat shrinkable PE/PP, PE/PET, PP/PP or others wherein the core component is composed of a high melting component as raw material, and treated with hot air, spun lace nonwoven fabric where fibers are confounded by water stream pressure, spun bond nonwoven fabric where continuous fibers are laminated and formed into a sheet, needle punch nonwoven fabric where fibers are confounded each other by a needle, SMS nonwoven fabric where spunbond and melt blown are laminated in multilayer and formed into a sheet, but also materials comprising a porous foam film, a film mainly composed PE resin, or others independently or in combination, can be cited.

Moreover, extensibility can be imparted to the aforementioned materials by engaging them between a male die and a female die, and the corrugation processing for impressing a shape by heat, temperature and pressure. To be more specific, a through air non-woven fabric comprising mainly composite synthetic fibers adjusted in a rage of 1.1 to 4.4 dtex in thickness, in a specific weight per unit area of 10 to 60 g/m.sup.2, submitted to the corrugation processing in a way extensible in the transversal direction can be cited. In the corrugation processing an array of male and female dies are installed so as to afford an extensibility of equal or superior to 10% and more preferably, in a range of 20 to 50%, and more preferably, those wherein the load under the 30% extension presents a behavior in a range of 0.01 to 0.05 N/25 mm are desirable (test conditions: velocity 100 mm/min, chuck interval 100 mm with an expansion tensile tester. It should be appreciated that, as other method for imparting extensibility, slit line, circular cutout, or other methods may also be used.

<Adhesive>

As adhesive for coupling (affixing) respective material, generally used hot melt type adhesives can be used, and as example, pressure-sensitive type hot melt adhesive and heat-sensitive type hot melt adhesive can be cited. The pressure-sensitive type hot melt adhesive can be obtained by taking a synthetic rubber resin such as styrene-isoprene-styrene block copolymer (SIS), styrene-butadiene-styrene block copolymer (SBS), styrene-ethylene-butadiene-styrene block copolymer (SEBS), styrene-ethylene-propylene-styrene block copolymer (SEPS), or others as principal component, and melt blending there a tackifier such as terpin resin, chlorophoium resin and a plasticizer such as wax. As example of heat-sensitive type hot melt adhesive, those wherein the base resin is mainly composed of an olefin base resin, such as poly-.alpha.-olefin can be cited. A variety of such adhesives exist; however, considering the application stability, it is preferable to use a heat-sensitive type hot melt. As heat-sensitive type hot melt adhesive presenting a high application stability, those obtained by melt blending 45 to 55 weight % of poly-.alpha.-olefin, 10 to 15 weight % of plasticizer and 35 to 45 weight % of tackifier can be cited. As for this heat-sensitive type hot melt, anti-oxidant, anti-fluorescent or others may be added in a range of 0.1 to 1.0 weight %.

[Structure of the Interlabial Pad Provided with Biodegradability, Water Dispersibility and Water Solubility]

Preferably the interlabial pad is comprised of a material of biodegradable rate and/or a material of water dispersible and/or a material of water-soluble. After using the pad comprised of these materials, it can be disposed into a toilet to flush, thereby the destruction of the pad can be easily and sanitarily achieved and the garbage in a toilet can be decreased.

In this Specification, "biodegradability" means that a substance is decomposed into gas such as carbon dioxide or methane, water, and biomass under anaerobic or aerobic condition according to the natural process under the existence of bacteria represented by actinomycetes and other microbes, and also means that the biodegradability (biodegradable rate and biodegradable degree) of the substance equals to a material naturally generated such as fallen leaves or a synthetic polymer generally recognized having the same biodegradability under the same environment. Water dispersibility" has the same meaning as water degradability. It means a characteristic in which, while having no influence when used in a limited amount of moisture (menstrual blood), in a large amount of water or water current, the fabric is easily dispersed into small pieces at least to a degree where an ordinal toilet plumbing is not clogged. "Water solubility" is a characteristic in which, while having no influence when used in a limited amount of moisture (menstrual blood), the fabric is soluble in a large amount of water or water current.

<Water Permeable Sheet>

As material that can be used for water permeable sheet, not only spun lace nonwoven fabric, wet spun lace nonwoven fabric selected from a range of 1 to 15 mm in fabric length can be used. As the other material, biodegradable resins by hydrolysis of poly lactic acid, polybutylene succinate or others may be used. For example, melt blown nonwoven fabric made using poly lactic acid as raw material and adjusted in a specific weight per unit area of 20 to 60 g/m.sup.2 or spunbond nonwoven fabric adjusted in a specific weight per unit area of 15 to 30 g/m.sup.2 and in a range of 1.1 to 3.3 dtex in fiber thickness can be cited. It should be appreciated that hole opening may or may not be exerted on respective nonwoven fabric.

As the other material, acetate, synthetic fibers can be used independently or ratan, continuous fibers of laminated elements, adjusted in a specific weight per unit area of 50 to 300 g/m.sup.2 can also be used by unlacing fibers each other.

<Absorbent Body>

As material that can be used for absorbent body, nonwoven fabric sheet obtained from the needling can be used. It should be appreciated that, considering the biodegradability or others of super absorbent polymer material, it is preferable to use carboxymethyl cellulose.

<Water Impermeable Sheet>

As material that can be used for water impermeable sheet, a PVA film, a PVA film sheet having one or both sides or a part thereof treated with water-repellent such as silicone, PVA films mixed with silicone, a starch film, a laminated paper laminated with a tissue and a film made from biodegradable resins by hydrolyzation such as polylactic acids, polybutylene succinates, etc. can be used. As necessary, mineral pigments may be blended in a range of 0.1 to 5% for coloration.

In case of considering the sustention of leak prevention under moisture and mitigation of excessive load to the septic tank, a laminate paper obtained by laminating a film using poly lactic acid as raw material with a tissue selected from a thickness range of 10 to 20 micron and in a specific weight per unit area of 15 to 20 g/m.sup.2, and the affixation area ratio for lamination is set in a range of 5 to 40% is preferable.

<Mini-Sheet>

Materials that can be used for mini-sheet include film using biodegradable resins such as poly lactic acid, polybutylene succinate or others, spunbond nonwoven fabric, melt blown nonwoven fabric or the like, or film, nonwoven fabric or others using PVA, CMC or other water soluble materials as raw material, and water dispersible tissue composed mainly of cellulose fiber, regenerated cellulose fiber or the like, spun lace nonwoven fabric or others.

Preferably, it concerns spun bond nonwoven fabric or melt blown nonwoven fabric composed mainly of biodegradable material, sheet adjusted in a range of 0.1 to 3 dtex in thickness, and in a specific weight per unit area of 15 to 40 g/m.sup.2, and they can be obtained by applying the aforementioned mechanical corrugation processing.

<Bonding Method>

As bonding method, adhesion by water soluble or water swelling polyvinyl alcohol or others, heat seal, or bonding by hydrogen bonding, or other bonding method can be used independently or in combination, as convenient.

INDUSTRIAL APPLICABILITY

As described hereinabove, according to the present invention, wearing mistake can be reduced considerably, because the wearer can fit easily an interlabial pad to an appropriate point between the labia. In addition, compared to the case of the prior art, the effect of preventing menstrual blood from soiling the fingertip during the wearing can be enhanced.

The invention claimed is:

1. An interlabial pad for absorbing body fluid having an elongated shape, comprising:
   a surface sheet disposed on a face of the interlabial pad so as to face a wearer's body;
   a back sheet disposed on an opposite face of the interlabial pad so as to face a wearer's garment;
   an absorbent body enveloped between the surface sheet and the back sheet;
   a mini-sheet extending from one lateral side to another lateral side of the interlabial pad and also having a length in a longitudinal direction of the back sheet;
   a cavity for finger insertion formed in between the back sheet and the mini-sheet; and
   a cavity opening for guiding a fingertip inserted therein to the remainder of the cavity, having a width of at least a fingerbreadth of a wearer,
   wherein the mini-sheet is provided so that it covers a finger application point that is in contact with a wearer's vagina; and
   wherein the mini-sheet is formed of a pair of flap portions extending from lateral sides of the interlabial pad, across the back sheet, the mini-sheet having an affixing portion at an end of each flap portion in order to affix the ends of the pair of flap portion to each other.

2. The interlabial pad of claim 1, wherein at least a part of the mini-sheet is stretchable or elastically extensible at least in respect to a lateral direction of the interlabial pad.

3. The interlabial pad of claim 1, wherein the mini-sheet has a length dimension at least 10% longer than that of the interlabial pad in the longitudinal direction of the interlabial pad.

4. The interlabial pad of claim 1, wherein a total circumferential length of the cavity opening is between 30 mm to 120 mm.

5. The interlabial pad of claim 1, wherein the back sheet of the interlabial pad is provided with microscopic protrusions and depressions.

6. The interlabial pad of claim 1, wherein an adhesive is applied to a part of the surface sheet of the interlabial pad to be in contact with a genital area of the wearer's body.

7. The interlabial pad of claim 1, comprising an upheaval area on the surface sheet, the upheaval area protruding toward the wearer's body along the longitudinal direction of the surface sheet.

8. The interlabial pad of claim 1, wherein the back sheet is made of moisture permeable material.

9. The interlabial pad of claim 1, wherein the pad is formed with at least one of biodegradable material, water-soluble material and water dispersible material.

10. The interlabial pad of claim 1, wherein said interlabial pad is an interlabial pad for incontinence.

11. The interlabial pad of claim 1, wherein said interlabial pad is an interlabial pad for absorbing vaginal discharge.

12. An interlabial pad manufacturing method for manufacturing the interlabial pad of claim 1, comprising:
   setting longer a pair of wings ordinarily disposed at both side portions of a sanitary napkin; and
   bonding said wings to form said mini-sheet.

13. The interlabial pad, according to claim 1, wherein the affixing portion comprises a notch at each end of a flap portion, the notch dividing each end into two separate tips, the tips of each end of a flap portion are cross-connected with each other so as to form the mini-sheet.

14. The interlabial pad, according to claim 1, wherein the affixing portion comprises an adhesive applied to one end of one flap portion, wherein the other end of the flap portion is overlapped on the adhesive so as to form the mini-sheet.

* * * * *